(12) United States Patent
Horn et al.

(10) Patent No.: US 6,465,175 B2
(45) Date of Patent: *Oct. 15, 2002

(54) OLIGONUCLEOTIDE PROBES BEARING QUENCHABLE FLUORESCENT LABELS, AND METHODS OF USE THEREOF

(75) Inventors: Thomas Horn, Berkeley, CA (US); Hartmut R. Schroeder, Franklin, MA (US); Brian D. Warner, Martinez; Ellen Fiss, Albany, both of CA (US); Todd Sells, Bellingham; Say-Jong Law, Westwood, both of MA (US)

(73) Assignee: Bayer Corporation, Tarrytown, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/146,157

(22) Filed: Sep. 3, 1998

(65) Prior Publication Data

US 2001/0009760 A1 Jul. 26, 2001

Related U.S. Application Data

(60) Provisional application No. 60/057,810, filed on Sep. 4, 1997.

(51) Int. Cl.$^7$ .......................... C12Q 1/68; C07H 21/00
(52) U.S. Cl. ...................... 435/6; 536/22.1; 536/25.3; 436/501
(58) Field of Search ............................ 435/6; 536/25.3, 536/22.1; 436/501

(56) References Cited

U.S. PATENT DOCUMENTS

| | | | |
|---|---|---|---|
| 4,774,339 A | 9/1988 | Haugland et al. | 548/405 |
| 4,820,630 A * | 4/1989 | Taub | 435/5 |
| 5,124,246 A * | 6/1992 | Urdea et al. | 435/6 |
| 5,187,288 A | 2/1993 | Kang et al. | 548/110 |
| 5,248,782 A | 9/1993 | Haugland et al. | 548/110 |
| 5,274,113 A | 12/1993 | Kang et al. | 548/405 |
| 5,433,896 A | 7/1995 | Kang et al. | 252/700 |
| 5,451,663 A | 9/1995 | Kang et al. | 530/367 |
| 5,616,464 A * | 4/1997 | Slbagli et al. | 435/6 |

FOREIGN PATENT DOCUMENTS

| | | |
|---|---|---|
| EP | 0 713 921 A2 | 5/1996 |
| EP | 0 808 829 A1 | 11/1997 |
| WO | WO 93/09185 | 5/1993 |
| WO | WO 96/15270 | 5/1996 |
| WO | WO 97/00967 | 1/1997 |

OTHER PUBLICATIONS

Cardullo et al., Proceedings of the National Academy of Science (USA), vol. 85, pp. 8790–8794, 1988.*
Davis et al., "Use of a High Affinity DNA Ligand in Flow Cytometry," *Nucleic Acids Res.* 25(4):702–706 (1996).
Ellwood et al., "Strand Displacement Applied to Assays with Nucleic Acid Probes," *Clin. Chem.* 32(9):1631–1636 (1986).
Lee et al., "Allelic Discrimination by Nick–Translation PCR with Fluorogenic Probes," *Nucleic Acids Res.* 21(16):3761–3766 (1993).
Mergny et al., "Fluorescence Energy Transfer as a Probe for Nucleic Acid Structures and Sequences," *Nucleic Acids Res.* 22(6):920–928 (1994).
Rudert et al., "Double–Labeled Fluorescent Probes for 5' Nuclease Assays: Purification and Performance Evaluation," *Bio Techniques* 22:1140–1145 (1997).
Saiki et al., "A Novel Method for the Detection of Polymorphic Restriction Sites by Cleavage of Oligonucleotide Probes: Application to Sickle–Cell Anemia," *Biotechnology* 3:1008–1012 (1985).
Tyagi et al., "Molecular Beacons: Probes that Fluoresce Upon Hybridization," *Nature Biotech.* 14:303–308 (1996).
Weier et al., "Quantitative DNA Fiber Mapping," *Human Molec. Genet.* 4(10):1903–1910 (1995).
Lee et al., "DNA Sequencing With Dye–Labeled Terminators and T7 DNA Polymerase: Effect of Dyes and dNTPs on Incorporation of Dye–Terminators and Probability Analysis of Termination Fragments," *Nucleic Acids Research* 20(10):2471–2483 (1992).
McGrath et al., "Fluorescent Ligands for the Study of Receptors," *Trends in Pharmacological Sciences* 17(11):393–399 (1996).

* cited by examiner

*Primary Examiner*—Ardin H. Marschel
(74) *Attorney, Agent, or Firm*—Reed & Associates; Dianne E. Reed; J. Elin Hartrum

(57) ABSTRACT

Methods are provided for reducing background signals encountered in nucleic acid hybridization assays and other assays that involve hybridization of a labeled oligomer to its complement. The method is premised on the significant reduction of signal generation that occurs when a quenchable dye-labeled oligomer forms a hybrid complex. In addition, a method is provided for enhancing the detectable signal emitted from an amplification multimer hybridized to an oligomer probe to which a quenchable dye has been conjugated through a linker such that the emission from the dye is not quenched upon hybrid complex formation. Novel oligonucleotide probes are also provided that comprise an oligomer to which has been directly or indirectly through a linker a quenchable dye.

29 Claims, 9 Drawing Sheets

SEQUENCE LISTING

```
<160> NUMBER OF SEQ ID NOS: 8

<210> SEQ ID NO 1
<211> LENGTH: 27
<212> TYPE: DNA
<213> ORGANISM: Unknown
<220> FEATURE:
<223> OTHER INFORMATION: Description of Unknown Organism:This
      information is not available.

<400> SEQUENCE: 1
tcccacatcc tattttcatt tgctcca                                           27

<210> SEQ ID NO 2
<211> LENGTH: 52
```

```
<212> TYPE: DNA
<213> ORGANISM: Unknown
<220> FEATURE:
<223> OTHER INFORMATION: Description of Unknown Organism:This
      information is not available.

<400> SEQUENCE: 2
gtggagcaaa tgaaatagg atgtgggata caggacgcct catggcgtcc tg          52

<210> SEQ ID NO 3
<211> LENGTH: 18
<212> TYPE: DNA
<213> ORGANISM: Unknown
<220> FEATURE:
<223> OTHER INFORMATION: Description of Unknown Organism:This
      information is not available.

<400> SEQUENCE: 3
aagtacgaca accacatc                                               18

<210> SEQ ID NO 4
<211> LENGTH: 23
<212> TYPE: DNA
<213> ORGANISM: Unknown
<220> FEATURE:
<223> OTHER INFORMATION: Description of Unknown Organism:This
      information is not available.

<400> SEQUENCE: 4
aagtacgaca accacatctt ttt                                         23

<210> SEQ ID NO 5
<211> LENGTH: 43
<212> TYPE: DNA
<213> ORGANISM: Unknown
<220> FEATURE:
<223> OTHER INFORMATION: Description of Unknown Organism:This
      information is not available.

<400> SEQUENCE: 5
gatgtggttg tcgtactttt tctcttggaa agaaagtgaa gtg                   43

<210> SEQ ID NO 6
<211> LENGTH: 60
<212> TYPE: DNA
<213> ORGANISM: Unknown
<220> FEATURE:
<223> OTHER INFORMATION: Description of Unknown Organism:This
      information is not available.

<400> SEQUENCE: 6
gatgtggttg tcgtacttga tgtggttgtc gtacttgatg tggttgtcgt acttgcgtag  60

<210> SEQ ID NO 7
<211> LENGTH: 12
<212> TYPE: DNA
<213> ORGANISM: Unknown
<220> FEATURE:
<223> OTHER INFORMATION: Description of Unknown Organism:This
      information is not available.

<400> SEQUENCE: 7
cagtcactac gc                                                     12

<210> SEQ ID NO 8
<211> LENGTH: 25
<212> TYPE: DNA
```

```
<213> ORGANISM: Unknown
<220> FEATURE:
<223> OTHER INFORMATION: Description of Unknown Organism:This
      information is not available.

<400> SEQUENCE: 8
tttctcttgg aaagaaagtg aagtg                                      25
```

OLIGONUCLEOTIDE PROBES BEARING QUENCHABLE FLUORESCENT LABELS, AND METHODS OF USE THEREOF

CROSS-REFERENCE TO RELATED APPLICATION

This application is related to provisional patent application serial No. 60/057,810, filed Sep. 4, 1997, from which priority is claimed under 35 USC §119(e)(1) and which is incorporated herein by reference in its entirety.

TECHNICAL FIELD

This invention relates generally to nucleic acid chemistry and hybridization assays. More particularly, the invention relates to a method for detecting a target nucleic acid in a sample using an oligonucleotide probe bearing a detectable label.

BACKGROUND

Nucleic acids have joined antigens and antibodies as key molecular targets for human diagnostic assays. In particular, due to the recent development of a variety of technical capabilities, microorganisms can now be detected and quantified at unprecedented low levels in clinical specimens.

A variety of concepts have provided the basis for a number of different probe-target hybridization detection systems.

Glazer et al. (1992) *Nature* 359:959 describe fluorescent intercalation complexes of polycationic ligands with double-stranded DNA (dsDNA) for high-sensitivity DNA detection. The fluorescent homodimers intercalate into dsDNA to form a complex that is stable to electrophoresis, thus allowing detection and quantitation of DNA after separation with minimum background interference.

Tyagi et al. (1996) *Nature Biotech.* 14:303–308 describe a probe that is optically silent in solution but fluoresce upon hybridization with a complementary target. The probe is a single-stranded oligonucleotide that possesses a stem-and-loop structure. The loop is a sequence complementary to the target. One arm of the stem has a fluorescent moiety attached and the other arm has a nonfluorescent quenching moiety attached. In the nonhybridized state, the stem keeps the two moieties in sufficiently close proximity so that the fluorescent moiety is quenched by the nonfluorescent moiety. Upon hybridization, the consonant conformational change in the probe forces the arm sequences apart and allows the fluorescent moiety to be detected.

Mergny et al. (1994) *Nucleic Acids Res.* 22:920–928 describes the use of fluorescence energy transfer to probe for primary or secondary structural features of single-stranded DNA. Two probes that hybridize to adjacent sequence of the target DNA respectively carry donor and acceptor dyes. Hybridization of the two probes to the target leads to fluorescence excitation energy transfer between the donor and acceptor dyes.

Davis et al. (1996) *Nucleic Acids Res.* 24:702–706 describe the use of DNA constructs containing one or two fluorescein molecules in flow cytometry. The fluorescein molecules were attached to the 3'-end of a DNA probe through an 18-atom spacer arm that resulted in a 10-fold increase in fluorescence intensity compared to the DNA probe to which fluorescein was directly attached to the 3'-end of the probe.

In addition, many forms of target amplification have been introduced for enhancing detection sensitivity since the polymerase chain reaction was first developed. These methods can be used for producing greater quantities of the target nucleic acid and assays using these methods generally use conventional detection schemes.

In contrast, direct analysis of target nucleic acids with great sensitivity has been accomplished using signal amplification. This method has been applied to the quantitation of many organisms and mRNAs. As few as 50 picomoles of the human immunodeficiency virus genome has been quantified in human plasma samples. The key molecule in the amplification method is a branched DNA (bDNA) that permits the specific incorporation of many labeled probes.

Two types of bDNA molecules have been used. The first type is a large network comprised of DNA oligomers assembled in solution from oligonucleotides containing three equally distributed $N^4$-[N-(6-aminocaproyl-2-aminoethyl)]-5-methyl-2'-deoxycytidine residues coupled to one another through homobifunctional amine-reactive cross-linking agents. Such "amplification multimer" (AM) networks permitted the specific hybridization of many alkaline phosphatase-labeled DNA probes per hybridization probe-target nucleic acid complex. These AMs gave significant signal amplification. As the multimer was increased in size, a limit to the signal amplification was achieved, possibly due to the location of complementary oligonucleotide sequences buried in the spherical cross-linked structure which may be inaccessible to the large alkaline phosphatase-labeled probes.

The second type of bDNA are "comb-type" molecules that comprise a linear primary oligonucleotide with a plurality of secondary side sequences having sites complementary to labeled DNA probes. As with the AMs, alkaline phosphatase-labeled DNA probes provide an amplified signal that does not match the theoretical signal amplification, possibly due to steric considerations.

The signal from fluorescently labeled DNA-probes can also be amplified using multiply labeled oligomers. However, due possibly to quenching effects, the incorporation of additional labels into a labeled probe does not produce a linear increase in fluorescent signal. For example, a two-fold increase in the number of labels per probe only yields a 1.2-fold increase in signal output. It would be possible to obtain an amplified fluorescent signal using a bDNA molecule as a scaffold for labeled DNA probes. However, again proximity of fluorophors may result in quenching-limited signal output. A highly sensitive fluorescent bDNA signal amplification-based assay would result if the quenching phenomenon were minimized.

SUMMARY OF THE INVENTION

The present invention provides methods and probes for detecting nucleic acid analytes in a sample. In general, the methods represent nucleic acid hybridization assays, such as fluorescent in situ hybridization assays, polymerase chain reaction assays, ligase chain reaction assays, competitive hybridization assays, strand displacement assays, and the like. In particular, the methods represent solution phase sandwich hybridization assays which involve binding the analyte to a solid support, labeling the analyte, and detecting the presence of label on the support. Preferred methods involve the use of amplification multimers which enable the binding of significantly more label in the analyte-probe complex, enhancing assay sensitivity and specificity. The probes comprise an oligonucleotide sequence to which has been conjugated, directly or indirectly through a linker, a dye that when in solution emits detectable radiation. Upon hybridization of the direct oligonucleotide-dye conjugate to a complementary oligonucleotide sequence the detectable radiation is substantially quenched. The detectable signal from an oligonucleotide-linker-dye conjugate is not appreciably quenched upon hybridization to a complementary oligonucleotide.

In a first aspect of the invention, a method is provide for detecting an oligonucleotide of interest in a sample. The method comprises (a) providing an oligonucleotide probe comprising (i) a nucleic acid sequence complementary to a nucleic acid sequence in the oligonucleotide of interest, and (ii) a label that, when the probe is in single-stranded, nonhybridized form, provides a detectable fluorescent signal, but which, when the probe hybridizes to a complementary nucleic acid strand, does not fluoresce, (b) combining the probe with the sample suspected of containing the oligonucleotide of interest under hybridizing conditions, while monitoring emitted fluorescence from the probe, and (c) correlating any decrease in fluorescence which occurs throughout step (b) with the presence or quantity of the oligonucleotide of interest.

In a related aspect of the invention, an improved solution phase sandwich hybridization assay for detecting an nucleic acid analyte in a sample, comprising: (a) binding the analyte indirectly to a solid support; (b) labeling the analyte; and (c) detecting the presence of label on the support, in which the improvement comprises incorporating a label probe system comprising (i) a label extender molecule having a first segment L-1 capable of hybridizing to a nucleic acid sequence in the analyte and a second segment L-2, (ii) an amplification multimer containing a nucleic acid sequence M-1 capable of hybridizing to nucleic acid sequence L-2 and a plurality of identical oligonucleotide subunits containing nucleic acid sequences M-2 capable of hybridizing to a label probe, and (iii) an oligonucleotide probe comprising a nucleic acid sequence L-3 capable of hybridizing to M-2 and a label coupled to the probe through a linker incapable of specifically hybridizing with a nucleic acid sequence in the analyte, the label extender or the amplification multimer.

The invention additionally encompasses an oligonucleotide probe comprising (i) a nucleic acid sequence complementary to a nucleic acid sequence in an oligonucleotide of interest, and (ii) a label that, when the probe is in single-stranded, nonhybridized form, provides a detectable fluorescent signal, but which, when the probe hybridizes to a complementary nucleic acid strand, does not fluoresce.

In addition, the invention encompasses a singly labeled oligonucleotide probe comprising (i) a single-stranded nucleic acid molecule comprising first and second complementary nucleotide sequences flanking a third nucleotide sequence that forms a loop structure when the first and second complementary nucleotide sequences hybridize with one another, wherein the third nucleotide sequence in the loop structure comprises a nucleotide sequence complementary to a nucleotide sequence in a target oligonucleotide, and (ii) a label that, when the first and second nucleotide sequences are hybridized to one another, is substantially quenched, and when the third nucleotide sequence is hybridized to the oligonucleotide of interest and the first and second nucleotide sequences are in nonhybridized form, provides a detectable fluorescent signal.

These and other embodiments of the present invention will readily occur to those of ordinary skill in the art in view of the disclosure herein.

DETAILED DESCRIPTION OF THE INVENTION

Definitions and Nomenclature

Figure 1:
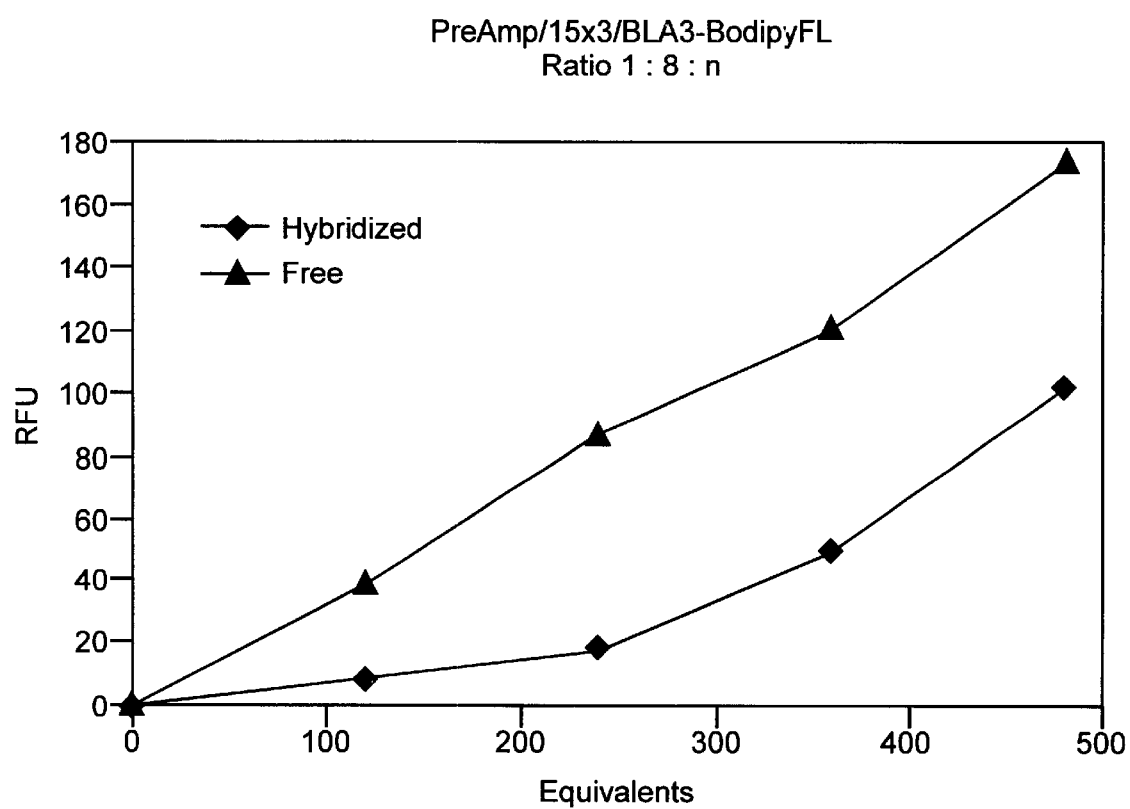
FIG. 1 is a graphical representation of the results of the experiment described in Example 3. The triangles represent the fluorescence obtained for a quenchable dye-labeled probe free in solution. The diamonds represent the fluorescence obtained for a quenchable dye-labeled probe-amplification multimer hybrid complex.

Before the present invention is disclosed and described in detail, it is to be understood that this invention is not limited to specific assay formats, materials or reagents, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a label probe" includes more than one label probe, reference to "a dye compound" includes more than one dye compound, reference to "a nucleic acid analyte" includes more than one such analyte, reference to "a nucleoside" includes more than one nucleoside, and the like.

In this specification and in the claims which follow, reference will be made to a number of terms which shall be defined to have the following meanings:

The term "quench" or "quenching" is used to indicate a reduction in detectable emission radiation, e.g., fluorescent or luminescent radiation, from a source that would otherwise have emitted this radiation. Quenching is a reduction of at least 50%, preferably 80% and more preferably 90%, of the detectable radiation from the source.

The term "quenchable dye" as used herein is a single molecular species that emits detectable radiation when in solution or bound to a single-stranded oligomer, either directly or through a linking moiety. The detectable radiation of a quenchable dye bound directly to a single-stranded oligomer is reversibly quenched upon hybridization of the oligomer to a complementary oligonucleotide to form a hybrid duplex or triplex. No additional molecular species, e.g., a quenching dye, is required for the quenching to occur. However, if the quenchable dye is bound to the oligomer through a linker moiety, hybridization of the oligomer to its complement will not result in quenching of the detectable radiation emitted by the dye.

As used herein, the terms "polynucleotide" and "oligonucleotide" shall be generic to polydeoxyribonucleotides (containing 2-deoxy-D-ribose), to polyribonucleotides (containing D-ribose), to any other type of polynucleotide which is an N- or C-glycoside of a purine or pyrimidine base, and to other polymers containing nonnucleotidic backbones, for example, polyamide (e.g., peptide nucleic acids (PNAs)) and polymorpholino (commercially available from the Anti-Virals, Inc., Corvallis, Oreg., as Neugene™ polymers), and other synthetic sequence-specific nucleic acid polymers providing that the polymers contain nucleobases in a configuration which allows for base pairing and base stacking, such as is found in DNA and RNA. There is no intended distinction in length between the term "polynucleotide" and "oligonucleotide," and these terms will be used interchangeably. These terms refer only to the primary structure of the molecule. Thus, these terms include, for example, 3'-deoxy-2',5'-DNA, oligodeoxyribonucleotide N3'→P5' phosphoramidates, 2'-O-alkyl-substituted RNA, double- and single-stranded DNA, as well as double- and single-stranded RNA, DNA:RNA hybrids, and hybrids between PNAs and DNA or RNA, and also include known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides will also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

Furthermore, modifications to nucleotidic units include rearranging, appending, substituting for or otherwise altering functional groups on the purine or pyrimidine base which form hydrogen bonds to a respective complementary pyrimidine or purine. The resultant modified nucleotidic unit may form a base pair with other such modified nucleotidic units but not with A, T, C, G or U. Standard A-T and G-C base pairs form under conditions which allow the formation of hydrogen bonds between the $N^3$-H and $C^4$-oxy of thymidine and the $N^1$ and $C^6$-$NH_2$, respectively, of adenosine and between the $C^2$-oxy, $N^3$ and $C^4$-$NH_2$, of cytidine and the $C^2$-$NH_2$, $N^1$-H and $C^6$-oxy, respectively, of guanosine. Thus, for example, guanosine (2-amino-6-oxy-9-β-D-ribofuranosyl-purine) may be modified to form isoguanosine (2-oxy-6-amino-9-β-D-ribofuranosyl-purine). Such modification results in a nucleoside base which will no longer effectively form a standard base pair with cytosine. However, modification of cytosine (1-β-D-ribofuranosyl-2-oxy-4-amino-pyrimidine) to form isocytosine (1-β-D-ribofuranosyl-2-amino-4-oxy-pyrimidine) results in a modified nucleotide which will not effectively base pair with guanosine but will form a base pair with isoguanosine. Isocytosine is available from Sigma Chemical Co. (St. Louis, Mo.); isocytidine may be prepared by the method described by Switzer et al. (1993) *Biochemistry* 32:10489–10496 and references cited therein; 2'-deoxy-5-methyl-isocytidine may be prepared by the method of Tor et al. (1993) *J. Am. Chem. Soc.* 115:4461–4467 and references cited therein; and isoguanine nucleotides may be prepared using the method described by Switzer et al. (1993), supra, and Mantsch et al. (1993) *Biochem.* 14:5593–5601, or by the method described U.S. Pat. No. 5,780,610 to Collins et al. The nonnatural base pairs referred to as κ and π, may be synthesized by the method described in Piccirilli et al. (1990) *Nature* 343:33–37 for the synthesis of 2,6-diaminopyrimidine and its complement (1-methylpyrazolo [4,3]-pyrimidine-5,7-(4H,6H)-dione. Other such modified nucleotidic units which form unique base pairs have been described in Leach et al. (1992) *J. Am. Chem. Soc.* 114:3675–3683 and Switzer et al., supra, or will be apparent to those of ordinary skill in the art.

The terms "polynucleotide analyte" and "nucleic acid analyte" are used interchangeably and refer to a single- or double-stranded nucleic acid molecule that contains a target nucleotide sequence. The analyte nucleic acids may be from a variety of sources, e.g., biological fluids or solids, food stuffs, environmental materials, etc., and may be prepared for the hybridization analysis by a variety of means, e.g., proteinase K/SDS, chaotropic salts, or the like. The term "polynucleotide analyte" is used interchangeably herein with the terms "analyte," "analyte nucleic acid" and "target."

As used herein, the term "target region" or "target nucleotide sequence" refers to a probe-hybridizing region contained within the target molecule. The term "target sequence" refers to a sequence with which a probe will form a stable hybrid under desired conditions.

As used herein, the term "probe" refers to a structure comprised of a polynucleotide, as defined above, that contains a nucleic acid sequence complementary to a nucleic acid sequence present in the target analyte. The polynucleotide regions of probes may be composed of DNA, and/or RNA, and/or synthetic nucleotide analogs.

It will be appreciated that the hybridizing sequences need not have perfect complementarity to provide stable hybrids. In many situations, stable hybrids will form where fewer than about 10% of the bases are mismatches, ignoring loops of four or more nucleotides. Accordingly, as used herein the term "complementary" refers to an oligonucleotide that forms a stable duplex with its "complement" under assay conditions, generally where there is about 90% or greater homology.

The terms "nucleic acid multimer" or "amplification multimer" are used herein to refer to a linear or branched polymer of the same repeating single-stranded oligonucleotide segment or different single-stranded polynucleotide segments, each of which contains a region where a labeled probe can hybridize, i.e., contains a nucleic acid sequence complementary to a nucleic acid sequence contained within a labeled probe; the oligonucleotide segments may be composed of RNA, DNA, modified nucleotides or combinations thereof. At least one of the segments has a sequence, length, and composition that permits it to hybridize specifically to a labeled probe; additionally, at least one of the segments has a sequence, length, and composition that permits it to hybridize specifically to a label extender or to a preamplifier system. Typically, such segments will contain approximately 15 to 50, preferably 15 to 30, nucleotides, and will have a GC content in the range of about 20% to about 80%. The total number of oligonucleotide segments in the multimer will usually be in the range of about 3 to 1000, more typically in the range of about 10 to 100, and most typically about 50. The oligonucleotide segments of the multimer may be covalently linked directly to each other through phosphodiester bonds or through interposed linking agents such as nucleic acid, amino acid, carbohydrate or polyol bridges, or through other cross-linking agents that are capable of cross-linking nucleic acid or modified nucleic acid strands. Alternatively, the multimer may be comprised of oligonucleotide segments which are in part covalently attached, but are also bonded in some other manner, e.g., through hybridization. Such a multimer is described, for example, in U.S. Pat. No. 5,175,270 to Nilsen et al. The site(s) of linkage may be at the ends of the segment (in either normal, 3'–5' orientation or randomly oriented) and/or at one or more internal nucleotides in the strand. In linear multimers the individual segments are linked end-to-end to form a linear polymer. In one type of branched multimer three or more oligonucleotide segments emanate from a point of origin to form a branched structure. The point of origin may be another nucleotide segment or a multifunctional molecule to which at least three segments can be covalently bound. In another type, there is an oligonucleotide segment backbone with one or more pendant oligonucleotide segments. These latter-type multimers are "fork-like," "comb-like" or combination "fork-" and "comb-like" in structure, wherein "comb-like" multimers, the preferred multimers herein, are polynucleotides having a linear backbone with a multiplicity of sidechains extending from the backbone. The pendant segments will normally depend from a modified nucleotide or other organic moiety having appropriate functional groups to which oligonucleotides may be conjugated or otherwise attached. The multimer may be totally linear, totally branched, or a combination of linear and branched portions. Typically, there will be at least two branch points in the multimer, more preferably at least three, more preferably in the range of about 5 to 30, although in some embodiments there may be more. The multimer may include one or more segments of double-stranded sequences. Further information concerning multimer synthesis and specific multimer structures may be found in commonly owned U.S. Pat. No. 5,124,246 to Urdea et al.

Commonly assigned U.S. patent application Ser. No. 07/813,588 and European Patent Publication No. 541,693 describe the comb-type branched multimers that are composed of a linear backbone and pendant sidechains; the backbone includes a segment that provides a specific hybridization site for analyte nucleic acid or nucleic acid bound to the analyte, whereas the pendant sidechains include iterations of a segment that provide specific hybridization sites for a labeled probe. A method of synthesizing a comb-type multimer is described below in the Experimental section.

As noted above, a "preamplifier system" may also be used, which serves as a bridging system between the label extender molecules and the amplification multimers. In this way, more amplifier and thus more label may be bound in any given target-probe complex. A preamplier system contains a "prepreamplifier molecule" and/or a "preamplifier molecule." Prepreamplifier molecules are designed to serve as a bridge between label extender molecules and preamplifier molecules, while preamplifier molecules are designed to serve as a bridge between either label extender molecules or prepreamplifier molecules and amplification multimers. Prepreamplifier molecules may be linear or branched, typically containing about 30 to about 3000 nucleotides, and comprise at least one segment having a sequence, length, and composition that permits it to hybridize specifically to a label extender and at least one segment that permits it to hybridize to a preamplifier molecule. Preamplifier molecules, in turn, may be either linear or branched, and typically contain in the range of about 30 to about 3000 nucleotides. In one preferred embodiment herein, a prepreamplifier or a preamplifier molecule hybridizes to at least two different label extender molecules, such that the overall accuracy of the assay is increased (i.e., because, again, a plurality of hybridization events are required for the probe-target complex to form).

As used herein, a "biological sample" refers to a sample of tissue or fluid isolated from an individual, including but not limited to, for example, plasma, serum, spinal fluid, semen, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components). Preferred uses of the present method are in detecting and/or quantitating nucleic acids as follows: (a) viral nucleic acids, such as from hepatitis B virus ("HBV"), hepatitis C virus ("HCV"), hepatitis D virus ("HDV"), human immunodeficiency virus ("HIV"), and the herpes family of viruses, including herpes zoster (chicken pox), herpes simplex virus I & II, cytomegalovirus, Epstein-Barr virus, and the recently isolated Herpes VI virus; (b) bacterial nucleic acids, such as Chlamydia, Mycobacterium tuberculosis, etc.; and (c) numerous human sequences of interest.

"Label extender molecules (LEs)," also referred to herein as "label extenders," contain regions of complementarity vis-à-vis the analyte polynucleotide and to the amplification multimer. If a prepreamplifier or a preamplifier is used, the label extender molecules will hybridize to this intermediate species rather than directly to the amplification multimer. If neither a preamplifier system nor an amplifier is used, the label extender molecules will hybridize directly to a sequence in the labeled probe ("LP"). Thus, label extender molecules are single-stranded polynucleotide chains having a first nucleic acid sequence L-1 complementary to a sequence of the analyte polynucleotide, and a second universal region having a multimer recognition sequence L-2 complementary to a segment M-1 of label probe, amplification multimer, prepreamplifier or preamplifier.

"Labeled probes (LPs)" are designed to hybridize either to the label extender, or, if an amplification multimer is employed in the assay, to the repeating oligonucleotide segments of the multimer. LPs either contain a label or are structured so as to hybridize to a label. Thus, LPs contain a nucleic acid sequence L-3 complementary to a nucleic acid sequence M-2 present within the repeating oligonucleotide units of the multimer and are bound to, or structured so as to hybridize to, a label which provides, directly or indirectly, a detectable signal.

"Capture extender molecules (CEs)," also referred to herein as "capture extenders," hybridize to the analyte polynucleotide and to capture probes, which are in turn covalently bound to a solid support. Thus, capture extender molecules are single-stranded polynucleotide chains having a first polynucleotide sequence region containing a nucleic acid sequence C-1 which is complementary to a sequence of the analyte, and a second, noncomplementary region having a capture probe recognition sequence C-2. The sequences C-1 and L-1 are nonidentical, noncomplementary sequences that are each complementary to physically distinct sequences of the analyte.

"Capture probes (CPs)" hybridize to the capture extenders and bind to a solid support. Capture probes have a nucleic acid sequence C-3 complementary to C-2 and are covalently bound to (or capable of being covalently bound to) a solid support.

Generally, solution phase hybridization capture assays are disclosed in U.S. Pat. No. 5,635,352 to Urdea et al., the disclosure of which in incorporated herein by reference, and proceed as follows. Single-stranded analyte nucleic acid is incubated under hybridization conditions with the capture extenders and label extenders. The resulting product is a nucleic acid complex of the analyte polynucleotide bound to the capture extenders and to the label extenders. This complex may be subsequently added under hybridizing conditions to a solid phase having the capture probes bound to the surface thereof; however, in a preferred embodiment, the initial incubation is carried out in the presence of the support-bound capture probes. The resulting product comprises the complex bound to the solid phase via the capture extender molecules and capture probes. The solid phase with bound complex is then separated from unbound materials. An amplification multimer, preferably a comb-type multimer as described above, is then optionally added to the solid phase-analyte-probe complex under hybridization conditions to permit the multimer to hybridize to the LEs; if a preamplifier system is used, the solid phase-analyte-probe complex is incubated with the preamplifier system probes either along with the amplification multimer or, preferably, prior to incubation with the amplification multimer. The resulting solid phase complex is then separated from any unbound preamplifier and/or multimer by washing. The labeled probes are then added under conditions which permit hybridization to LEs, or, if an amplification multimer was used, to the repeating oligonucleotide segments of the multimer. The resulting solid phase labeled nucleic acid complex is then washed to remove unbound labeled oligonucleotide. A label probe to which a quenchable dye has been conjugated will not emit a detectable signal while hybridized to an LE or an amplification multimer, as described more fully below. Thus, the label probe is then dissociated from the hybrid complex with the LE or amplification multimer by any method well known in the art, e.g., by warming, by the addition of a detergent or high salt, and the like. The signal from the dissociated label probe can then be read.

One primary focus of the present invention is on minimizing background noise by employing a probe that emits a detectable signal only under desired conditions. Another primary focus of the invention is to provide a signal amplification system that produces a greater yield of detectable signal than possible with previous systems.

The inventors herein have observed that when an oligomer, directly labeled with a quenchable fluorescent dye, hybridizes to a complementary nucleotide sequence, substantial quenching occurs relative to the fluorescence observed for the same amount of probe free in solution (see Example 1). As exemplified below, nucleic acid hybridization assays having reduced background noise by, for example, producing a detectable signal only upon dissociation of a directly labeled probe from its complement are a significant improvement over conventional assay methods.

In addition, it has now been observed that quenching can be substantially reduced by coupling a quenchable dye to an oligomer through a linker (see Example 3). This provides a means to enhance signal amplification through the use of branched DNA amplification multimers. Conventional fluorescent oligomer label probes having multiple labels per probe, tend to "self-quench," thereby limiting fluorescent signal emission. In addition, when a plurality of fluorescent label probes are hybridized to an amplification multimer containing a plurality of sequences complementary to the label probe, intramolecular quenching can occur. By contrast, hybridization of label probes comprising a quenchable dye compound indirectly conjugated to an oligomer as disclosed and claimed herein to an amplification multimer does not appear to result in self-quenching and yields an increased signal output.

Preferred quenchable dyes are fluorescent dipyrrometheneboron difluoride dyes having the chemical structure

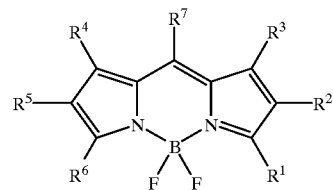

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX=CY—Z wherein X, Y and Z are independently halogen, $C_1$-$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

These compounds are described in U.S. Pat. Nos. 4,774,339 to Haugland et al., 5,187,288 to Kang et al., 5,248,782 to Haugland et al., 5,274,113 to Kang et al., 5,451,663 to Kang et al., and 5,433,896 to Kang et al., the disclosures of which are incorporated herein by reference. In particular, U.S. Pat. No. 5,541,663 describes fluorescent derivatives of dipyrromethenoboron difluoride dyes that are chemically reactive with biologically derived or chemically synthesized macromolecules to form dye-conjugates. Methods by which these fluorescent dyes may be synthesized and methods by which the dyes may be conjugated to biologically derived or synthetic chemical materials are also described in the Haugland et al. and Kang et al. patents cites herein. Many dipyrromethenoboron difluoride dyes useful in the invention are commercially available from Molecular Probes, Inc. (Eugene, Oreg.).

A particularly preferred dipyrromethenoboron difluoride dye is

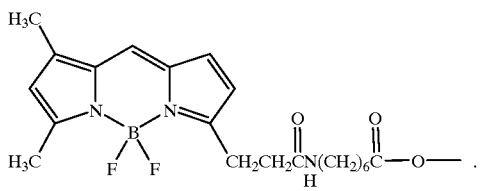

The dye may be conjugated directly to the oligomer or indirectly through a linker moiety. Oligomer-dye conjugates may be formed using conventional methods well known in the art.

The linker is a moiety that serves to connect the oligonucleotide probe to the label, covalently bound to both the probe and the label and having a molecular structure such that a desired degree of spacing is provided between the probe "backbone" and the label. Generally, the linker moiety is of a length sufficient to overcome the quenching effect of hybridization of the oligomer-label conjugate on the emission signal of the label. The linker may be a nucleic acid sequence, an amino acid sequence, a hydrocarbon chain, or the like. Preferably, the linker moiety is a nucleic acid sequence at least three or more nucleotides in length, more preferably between three and nine nucleotides in length. In addition, it is preferred that the linker moiety not hybridize under standard hybridizing conditions to either (a) the nucleic acid sequence complementary to the label probe, or (b) the target nucleotide sequence. An additional preferred linker moiety is an ethylene glycol or triethylene glycol linker of three or more, preferably three to nine, ethylene glycol or triethylene glycol units. The linker moiety may be conjugated to the 5' or 3' end of the oligomer or to an internal nucleoside having suitably reactive side group.

In addition, the dye compound may be incorporated into an oligomer by covalent attachment to a derivatizable nucleotide. A modified nucleotide that has a derivatizable site to which a label may be attached, and oligomers containing such a modified nucleotide, are disclosed in U.S. Pat. Nos. 4,910,300, 5,093,232, and 5,594,118 to Urdea et al., and 5,580,731 and 5,591,584 to Chang et al. For example, the N-4 modified pyrimidines of the Chang et al. '731 patent can be labeled at the N-4 position or at the 3' position.

As exemplified below, quenchable dye-oligomer conjugates are useful in a number of nucleic acid hybridization methods, including but not limited to solution-phase and solid-phase nucleic acid hybridization assays, in situ hybridization mapping, point mutation detection, and the like.

EXPERIMENTAL

The practice of the present invention will employ, unless otherwise indicated, conventional techniques of synthetic organic chemistry, biochemistry, molecular biology, and the like, which are within the skill of the art. Such techniques are explained fully in the literature. See, e.g., Sambrook, Fritsch & Maniatis, *Molecular Cloning: A Laboratory Manual*, Second Edition (1989); *Oligonucleotide Synthesis* (M. J. Gait, ed., 1984); *Nucleic Acid Hybridization* (B. D. Hames & S. J. Higgins, eds., 1984); and the series, *Methods in Enzymology* (Academic Press, Inc.).

It is to be understood that while the invention has been described in conjunction with the preferred specific embodiments thereof, that the description above as well as the examples which follow are intended to illustrate and not limit the scope of the invention. Other aspects, advantages and modifications within the scope of the invention will be apparent to those skilled in the art to which the invention pertains.

In the following examples, efforts have been made to ensure accuracy with respect to numbers used (e.g., amounts, temperature, etc.) but some experimental error and deviation should be accounted for. Temperature is always given in degrees C and, unless otherwise indicated, pressure is at or near atmospheric.

General Methods

Polyacrylamide gel electrophoresis (PAGE) analysis: Native 10% polyacrylamide slab gels were prepared using a solution containing 10 ml of a 40% stock solution (Amresco, cat. no. 0496), 30 ml of 1× Tris-borate buffer ("TBE") (100 mM Tris-borate, 1 mM EDTA, 7 M urea, pH 8.3), 0.4 ml 10% ammonium persulfate and 20 $\mu$l N,N,N',N'-tetramethylethylenediamine. A 0.5 mm slab was poured between 20 cm×20 cm plates, and a comb with 10 1-cm teeth was inserted between the plates to form loading wells. After prerunning the gel at 25 mAmp for 20 min at 4° C. and prewashing the loading wells, sample mixtures were loaded into the wells. The sample mixtures consisted of 5 $\mu$l sample, 5 $\mu$l 15% (w/v) Ficoll and 0.05% bromophenol blue (BPB) in water. The gel were run at 25 mAmp at 4° C. Bands were visualized by transferring the gel to a silica gel thin layer chromatography plate with a fluorescent indicator on the glass (Merck silica gel 60 $F_{254}$) which had been covered with plastic wrap. DNA bands were visualized by UV shadowing, i.e., by exposing the gel on the plate to ultraviolet light at 260 nm. Fluorescent bands were visualized by exposing the gel on the plate to 360-nm light.

Oligonucleotide Synthesis: Oligodeoxynucleotides were synthesized by standard solid-phase chemistry using 2-cyanoethyl phosphoramidite monomers. The phosphorylating reagent 2-((2-((4,4'-dimethoxytrityl)oxy)ethyl) sulfonylethyl-2-cyanoethyl-N,N-diisopropylphosphoramidite (Phostel) was used to synthesize both 3'- and 5'-phosphorylated oligomers.

Conjugation of dye compounds to an oligonucleotide probe to form the label probe: The 3'-long chain amine ("LCA") portion (L) of the bla3 oligonucleotide (5'-AAG TAC GAC AAC CAC ATC L-3'), SEQ ID NO:3 wherein L is $N^4$-(6-aminocaproyl-2-aminoethyl)-5-methyl-2'-deoxycytidine, was reacted with the carboxylated dye molecule in a 1:100 ratio of BLA3:dye. Thus, the dye N-hydroxysuccinimide ester and BLA3 were added to 100 mM phosphate buffer, pH 7.8, and incubated for 3 hr at room temperature.

The reaction mixture was applied to a NAP-5 column (Pharmacia) previously equilibrated with water and eluted with water. The desired product is isolated by PAGE. The product band is cut from the gel, crushed and extracted using 0.5 M NaCl, 100 mM Tris, pH 8.3, 10 mM $MgCl_2$, desalted and ethanol precipitated. A BODIPY® FL LCA-nucleoside has the following structure:

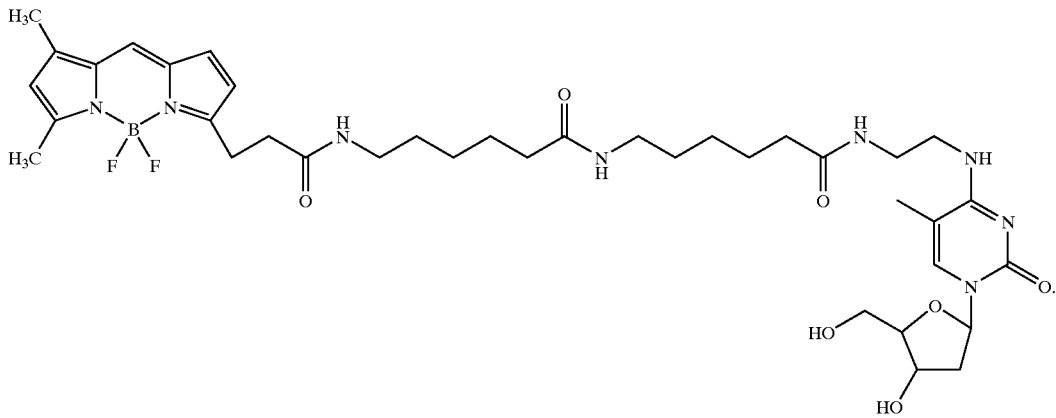

If desired, the oligomer-dye conjugate may be further purified using, for example, ion exchange chromatography, hydrophobic chromatography, reverse phase chromatography, chromatofocusing or affinity chromatography. The ratio of label to DNA is determined using analytical gel electrophoresis.

EXAMPLE 1

Fluorescence Quenching Upon Hybridization of a Labeled Probe to a Linear Oligonucleotide The functional properties of branched DNA amplification multimers were examined with two fluorescence techniques: a solution phase hybridization-dependent quenching test and a gel shift polyacrylamide analytical test.

A series of reaction mixtures each having a final volume of 5 μl in 1× SSC was made containing 0–100 pmoles of each of the following components: (1) the amplification multimer prepared as described in Example 1; (2) 5'-BLA3-3'-dye or dye-5'-BLA3; and (3) 5'-BLA3c-PSCPc-3'. BLA3 is the oligomer 5'-AAG TAC GAC AAC CAC ATC TTT TT-3' SEQ ID NO:4 and BLA3c-PSCPc is the oligomer 5'-GAT GTG GTT GTC GTA CTT TTT CTC TTG GAA AGA AAG TGA AGT G-3', SEQ ID NO:5 wherein complementary oligomer segments are underlined. The reaction mixture was heated in a waterbath at 60° C. for 15 min, then cooled to room temperature. The samples were diluted with 5 μl 15% (w/v) Ficoll/0.05% BPB in water then loaded into the wells of a 10% native PAGE gel (20×20 cm poured without urea). The gel was electrophoresed until the tracer dye (BPB) had migrated about ⅔ down the gel The bands were visualized by UV shadowing. The gel was transferred to a 20×20 cm silica gel thin layer chromatography plate (E. Merck silica gel 60 $F_{254}$ with fluorescent indicator on glass) which had been covered with plastic wrap. The gel/plate was exposed to UV light at 260 nm to visualize the DNA bands, and at 360 nm to visualize fluorescent bands. The 15×3 amplification multimer and the 15×3 amplification multimer/5'-BLA3-$T_5$-3'-BODIPY® FL hybrids did not migrate into the gel, whereas the 5'-BLA3-$T_5$-3'-BODIPY® FL migrated slightly ahead of the BPB dye.

A series of probes was synthesized with sequences complementary to repeated 18-nucleic acid sequences in a 60-mer. Each probe was labeled with BODIPY® FL (Molecular Probes, Eugene, Oreg.), fluorescein or Texas Red. The individual probes were hybridized to a linear complementary sequence and analyzed by native PAGE to determine the fluorescence properties of the labeled oligomers. In all cases quantitative hybrid formation was achieved as determined by the complete disappearance of free labeled probes, but the observed fluorescence intensity varied. Extensive quenching was observed with the BODIPY® FL-labeled oligomer, in contrast to the fluorescein- and Texas Red-labeled oligomers which did not show an noticeable quenching under the same hybridization conditions. The BODIPY® FL dye was thus sensitive to the environment of the labeled oligomer, and quenching was a measure of the proportion of the probe that had hybridized with its complement to form a DNA duplex.

When the BODIPY® FL was linked to the probe through a T-T-T-T-T ($T_5$) linker at the 3' end of the probe, essentially no quenching was observed upon hybridization of the probe to its complement.

EXAMPLE 2

Synthesis of a 15-Site Branched Comb DNA (bDNA) and Assembly into an Amplification Multimer A branched comb DNA having 15 branch sites to which was attached secondary sequences having three 18-mer hybridization sites complementary to a detectable label probe was prepared as follows.

A. Synthesis of the primary sequence. Controlled pore glass (CPG) solid support (2000 Å pore size) derivatized with 14.8 μmol/gm of dimethyltritylthymidine through an N-succinyl-aminopropyl linker (40.5 mg, 0.6 μmol) was packed into a column. The primary sequence was synthesized on an automated DNA synthesizer (Model 380B, Applied Biosystems Division, Perkin Elmer, Foster City, Calif.). The detritylation step used two 7-second pulses of trichloroacetate/$CH_2Cl_2$ (3% v/v), each followed by a 4-second pause, then the column was flushed. This process was repeated two more times. The phosphoramidite reagent (18 μmol of a 90 mM solution in acetonitrile) was used for each coupling of A, G, C, or T; however, for the branching monomer (N-4-(6-hydroxyhexyl)-5-methyl-2'deoxycytosine) phosphoramidite 20 μmol of a 100 mM solution in acetonitrile was used for each coupling.

B. Removal of levulinate protecting group of the branching monomer. The CPG from the primary synthesis was attached to a 10 ml plastic syringe and rinsed with 10 ml acetic acid/pyridine (1:1, v/v). Approximately 11 ml of 0.5 M hydrazine hydrate in acetic acid/pyridine was periodically pushed through over a period of 90 minutes at room temperature. The solid support was then rinsed with 10 ml of the acetic acid/pyridine, detached from the syringe, and followed by extensive rinsing with acetonitrile before brief drying under vacuum.

C. Synthesis of the secondary sequence. All reagents used to synthesize the secondary sequence were the same as in the primary sequence; however, their quantities differed. The detritylation process used three 8-second pulses of trichloroacetate solution, each followed by a 4-second pause, followed by a 20-second rinse (a 15-second pulse with a 5-second pause) of toluene/$CH_2Cl_2$ (1:1, v/v). This process was repeated two more times. Nucleoside phosphoramidite (96 μmol) was used for each coupling of A, C, G, or T. The coupling process consisted of an 8-second addition of activator, an 8-second addition of activator and phosphoramidite, followed by a 30-second wait. This was performed a total of 8 times. The capping and oxidation process each used two 10-second pulses of reagents separated by a 5-second pause, and then followed by a 60-second wait step. If the 5' ends of the secondary sequence required phosphorylation, then they were coupled with Phostel phosphoramidite (107 μmol each at 100 mM) with no capping between couplings.

D. Deprotection and Purification of the 15-site bDNA. The detritylated bDNA was cleaved with 2 ml 30% $NH_4OH$ for 45 min at room temperature. The supernatant was collected in a 4-ml glass vial which was capped and heated in a 60° C. oven for at least 16 hours, then dried under a vacuum. The crude bDNA was purified on a 7% T, 5% C polyacrylamide gel (20×40×1.5 cm) containing 7 M urea. The gel was run until the bromophenol blue dye migrated to within 2–3 cm of the bottom. The product band was excised and soaked in a 100 mM Tris-HCl buffer, pH 8.0 with 0.5 M NaCl and 5 mM EDTA for at least 24 hours with agitation. The salt was removed by loading the bDNA solution onto a short C-18 column and rinsing it with water. The purified bDNA was eluted from the column with methanol/$H_2O$ (1:1, v/v). After being dried and reconstituted in water, the bDNA was precipitated from ethanol/0.3 M aqueous potassium acetate (3:1, v/v).

E. Enzymatic Assembly of 15×3 bDNA Amplification Multimer. The 15-site bDNA comb oligomer (1 nmole), containing the 5'-p-TGA CTG-3' secondary sequence, and linear DNA sequences 5'-(GAT GTG GTT GTC GTA CTT)$_3$-GCG TAG-3' SEQ ID NO:6 (60-mer, 18.75 nmole) were combined with the linear DNA linker 5'-CAG TCA CTA CGC-3' (12-mer, 18.75 nmole) in a reaction tube in a total volume of 140 μl, and 25 μl ligation buffer (10× buffer: 500 mM Tris, pH 7.5, 100 mM $MgCl_2$, 20 mM spermidine) was added. The tube was heated to 95° C. and then slowly cooled to room temperature. At this point ATP (5 μl of 0.1 M), polyethylene glycol 8000 (70 μl of a 50% solution) and T4-ligase (6.7 units/μl, 50 units total) were added. This reaction was incubated at room temperature overnight. Sodium chloride was added (16.5 μl of 4 M) and ice-cold ethanol (800 μl) was added. The mixture was kept at −20° C. for 30 minutes and then centrifuged at 12,000×g for 30 min. The supernatant was decanted and the precipitate was first gently dried in vacuo and then resuspended in water. The product was purified as described above for the 15-site bDNA comb oligomer.

EXAMPLE 3

Solution Phase Hybridization to a 15×3 Amplification Multimer: Effect of Interposing a Linker Between the Probe and the Fluorophor The number of hybridizable BLA3c 18-mer sequences SEQ ID NO:7 in the amplification multimer containing 15 branches, each of which has three BLA3c sequences (a 15×3 bAM) was determined using BODIPY® FL hybridization-dependent quenching. Increasing amounts of BLA3-3'-BODIPY® FL (0 to 60 pmoles) were incubated with the 15×3 amplification multimer. After hybridization and dilution, the fluorescence was measured. The results of this experiment are shown in FIG. 1.

A standard curve for labeled probe alone was constructed and shown to have a linear response with increasing probe concentration. In contrast, when the same amounts of BLA3-3'-BODIPY® FL were hybridized to the 15×3 amplification multimer the resulting curve had two distinct slopes. At lower concentrations of labeled probe the fluorescence output was quenched by about 80% and showed a flat slope. On addition of more labeled probe the slope changed to parallel that of the free nonhybridized labeled probe, suggesting saturation of hybridizable sites. From the interception of the two linear regions it was determined that the 15×3 amplification multimer contained an average of 36 hybridizable sites, or 12 60-mer sequences.

Figure 2:
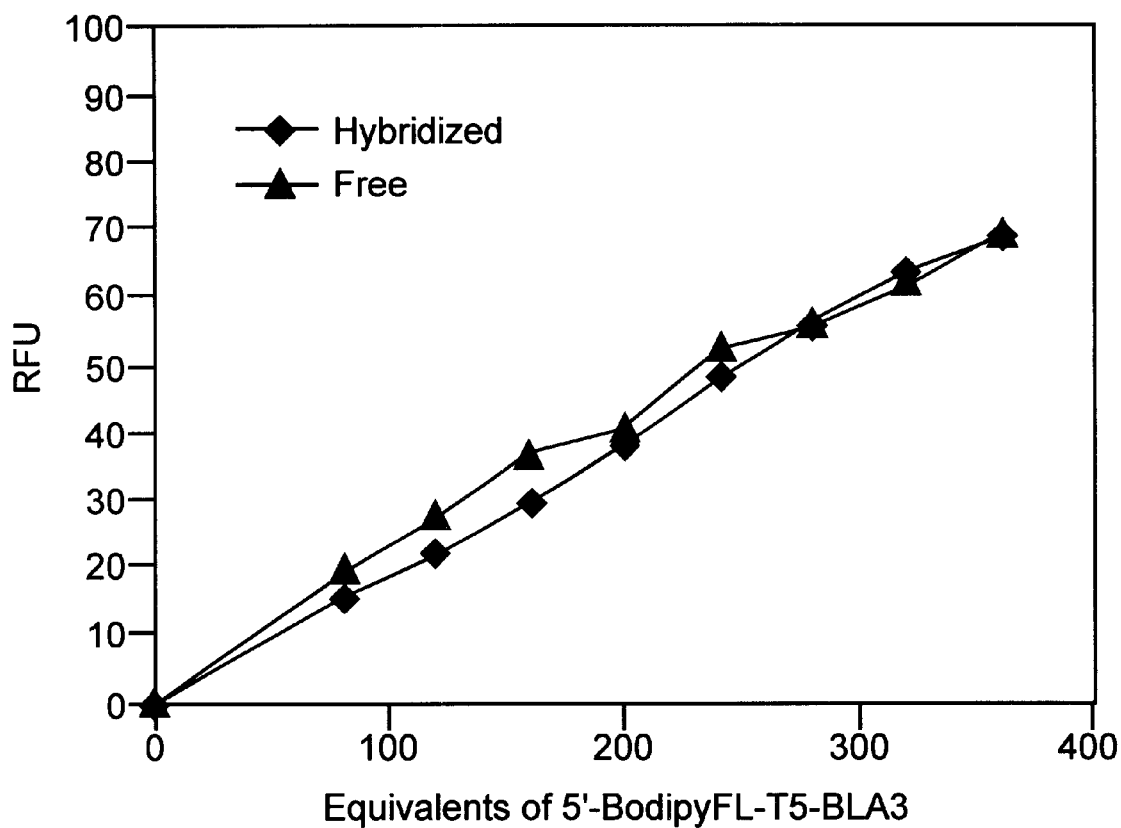
FIG. 2 is a graphical representation of the results of the experiment described in Example 3 in which a quenchable dye is conjugated to an oligomer probe through a $T_5$ linker. The triangles represent the fluorescence obtained for a quenchable dye-labeled probe free in solution. The diamonds represent the fluorescence obtained for a oligomer-3'-$T_5$-quenchable dye-labeled probe-amplification multimer hybrid complex.

The hybridization experiment was repeated substituting BLA3-$T_5$-3'-BODIPY® FL for the BLA3-3'-BODIPY® FL. $T_5$ indicates a nucleotide spacer of 5 lined thymidines to which the dye is linked to the 3'-end of the BLA3 oligomer. In contrast to the results obtained using the BLA3-3'-BODIPY® FL probe, quenching was not observed using the BLA3-$T_5$-3'-BODIPY® FL probe. The two curves, depicted in FIG. 2, relative fluorescence from hybridized and non-hybridized labeled probe, were essentially superimposable.

This observation further suggested that the 15×3 amplification multimer provides a scaffold that could accommodate hybridization of multiple labeled probes without internal quenching. This would be consistent with previous reports that have noted that energy transfer between fluorophors occurs when labels are placed within 9 to 18 base pairs of each other. The length and rigidity of the linkage between the oligomer and the label also affected quenching between chromophors. Morrison (1995) in Kricka (ed.), *Nonisotopic Probing, Blotting, and Sequencing* (Academic Press, NY), pp. 430–471. The 15×3 amplification multimer and the $T_5$-modified labeled probe formed hybrids that provided rigid spacing of more than 18 base pairs between dye molecules.

EXAMPLE 4

Solution Phase Hybridization to a 15×3 Amplification Multimer with PAGE Detection:

Effect of Interposing a Spacer Between the Oligomer Probe and the Fluorescent Dye The hybridization properties of BODIPY® FL conjugates probes were examined as described in Example 3 using native PAGE analysis, which does not destabilize oligonucleotide hybrids during electrophoresis. The 15×3 amplification multimer was allowed to hybridize with increasing amounts of BLA3-$T_5$-3'-BODIPY® FL. The free labeled probe migrated into the gel; the 15×3 amplification multimer was too large to enter the gel. The gel analysis showed that when the BODIPY® FL-labeled probe was fully hybridized to the amplification multimer, all fluorescence was retained in the loading well and did not migrate into the gel. As the amount of probe was increased beyond saturation of all hybridizable sites on the 15×3 amplification multimer, excess fluorescent probe migrated into the gel. The breakthrough when free probe started to migrate into the gel corresponded to approximately 35 hybridizable sites. The specificity of the hybridization was further demonstrated when the same modified labeled probe was incubated with a 15×3 amplification multimer that contained a noncomplementary sequence. All of the labeled probe was seen to migrate into the gel and none of the fluorescence was retained in the loading well.

EXAMPLE 5

Single Label-Quenching PCR Using Fluorogenic Probes

Figure 3A:
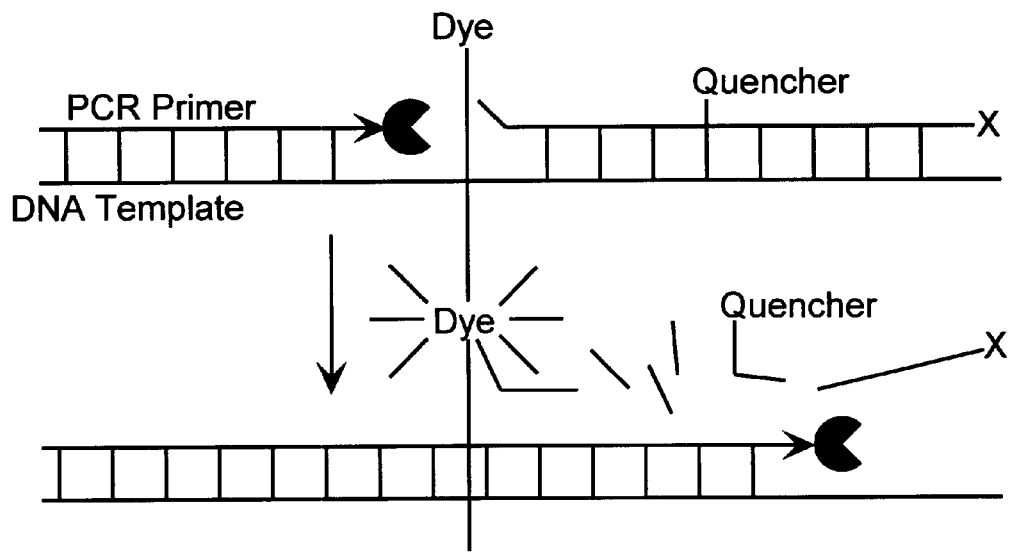
FIGS. 3A and 3B (SEQS IDS NO:1 & 2) are illustrations depicting the use of doubly labeled fluorogenic probes in nick-translation PCR and in 5' nuclease assays, respectively, as described in Example 5.

Lee et al. (1993) *Nucleic Acids Res.* 21:3761–3766 describe the use of a doubly labeled probe to monitor the results of nick-translation PCR to discriminate between alleles. In this method, a probe labeled at 5'-end with fluorescent-phosphoramidite and at 3'-end with amino modifier C6 dT Linker (Glen) and 3'-phosphate. An oligomer probe is converted to a double-labeled oligomer with 5'-6-carboxyfluorescein, or 5'-TET and 3'-6-carboxytetramethyl rhodamine, a quencher dye. The labeled probe is designed to anneal to a region of one strand of a PCR product downstream from one of the PCR primers. The 3' end of the probe is blocked from extension by the 3' phosphate. The probe is included with the other PCR reagents, e.g., dNTPs, and is degraded by the 5'→3' exonuclease activity inherent in Taq polymerase as the primer is extended in every cycle. Because the probe is doubly labeled, i.e., has a fluorophor at the 5' end and a quencher at the 3' end, the fluorescence of the indicator dye is quenched. An illustration of this method is provided in FIG. 3A. Probe digestion during PCR restores indicator dye fluorescence if and only if nucleolytic cleavage occurs between the two dyes. The degradation of two probes of different sequence can be monitored simultaneously if the two indicator dyes are spectrally distinguishable.

Figure 3C:
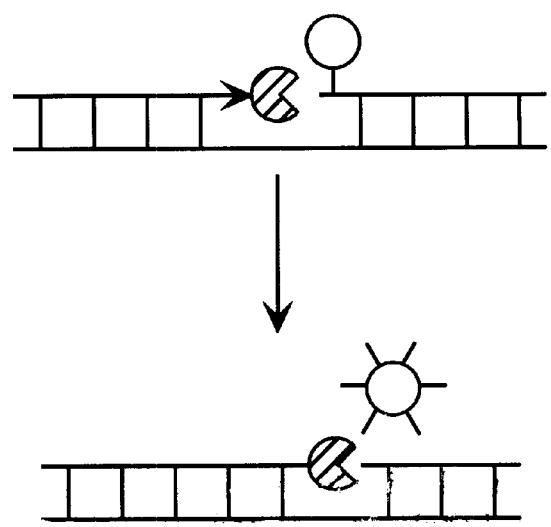
FIG. 3C is an illustration of the use of a probe labeled with a single quenchable dye species in a Taq polymerase-based assay system as described in Example 5.
Figure 3B:
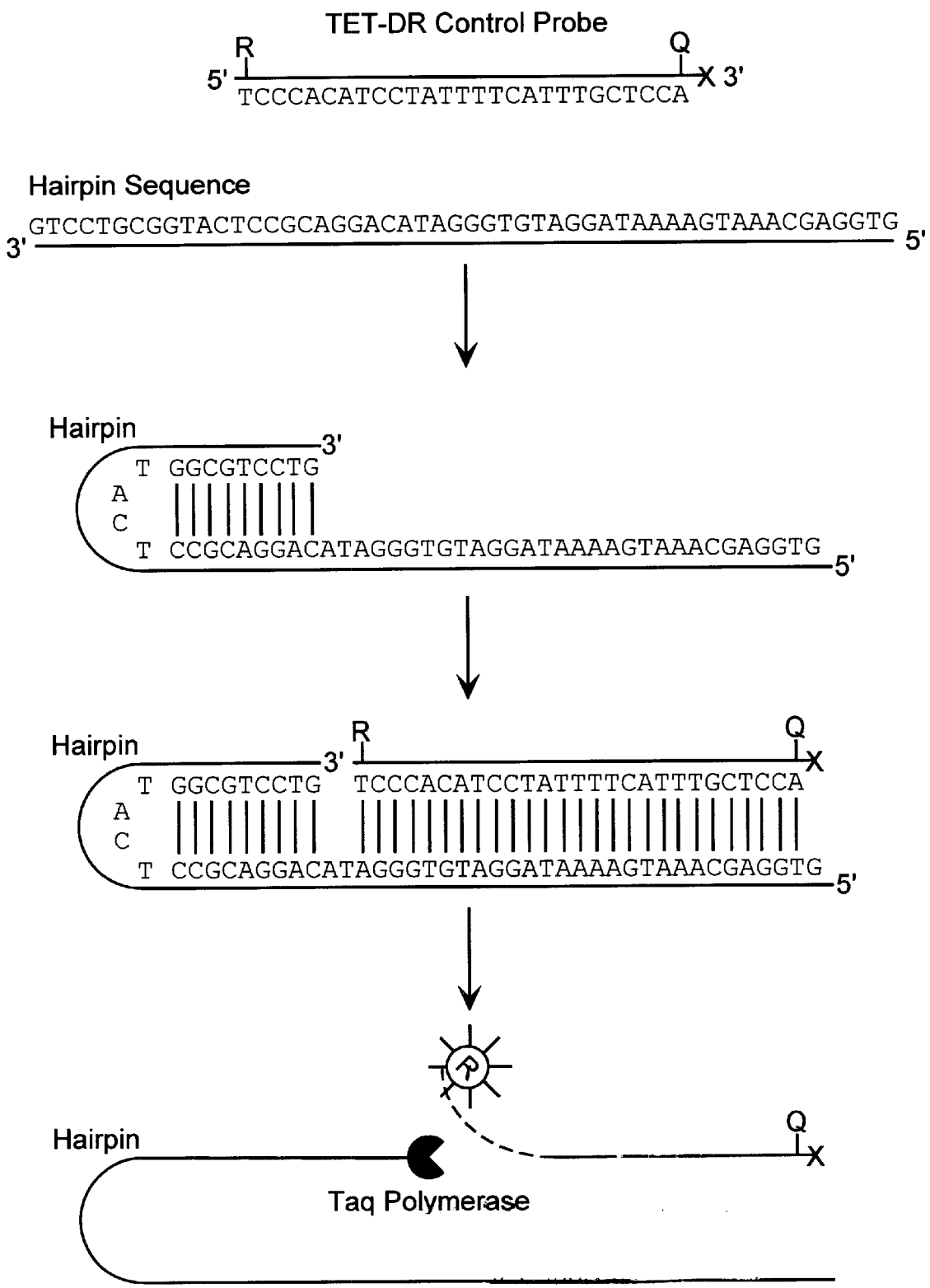

Rudert et al. (1997) *BioTechniques* 22:1140–1145 describes the use of similarly doubly labeled probes in 5' nuclease assays. A primer oligomer containing a hair-pin sequence and an oligomer probe having a 5'-fluorophor and a 3'-quencher are used. The primer forms a spontaneous hair-pin at the 3' end and hybridizes to the complementary sequence within the fluorescent probe. Due to the presence of the quencher, the fluorophor is not detectable when the probe is hybridized to the primer. In addition, upon hybridization, there is a two-nucleotide gap between the hair-pin primer and the probe. Taq polymerase extends the 3' end of the primer and cleaves the 5' end of the probe, liberating the reporter dye from the quenching effect of the 3' quenching dye. This system is illustrated in FIG. 3B.

In either of these methods by which the activity of a nucleotide polymerase may be monitored, an oligonucleotide singly labeled with BODIPY® FL or other quenchable dye as defined herein at the 5'-terminal nucleotide will hybridize to a target sequence and the fluorescence will be quenched without the use of a quencher dye. Taq polymerase will digest the probe from the 5'-end and release a 5'-BODIPY® FL-nucleotide, thus overcoming the quenching and producing a detectable signal. This system is illustrated in FIG. 3C.

EXAMPLE 6

Single Label Quenching Molecular Beacon

A Molecular Beacon system reports the presence of specific nucleic acids in homogeneous solution. These probes undergo a spontaneous fluorogenic conformational change when they hybridize to their target. Only perfectly complementary targets elicit this response, as hybridization does not occur when the target contains a mismatched nucleotide or a deletion. The probes can be used to monitor the synthesis of specific nucleic acids in real time. When used in nucleic acid amplification assays, gene detection is homogeneous and sensitive, and can be carried out in a sealed tube. See, Tyagi et al. (1996) *Nature* 14:303–308.

Figure 4A:
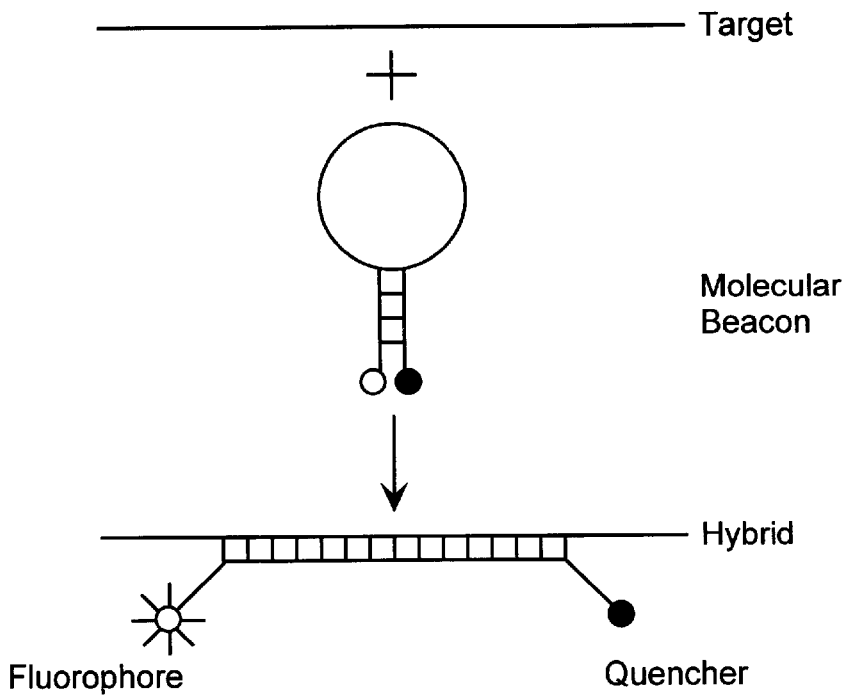
FIGS. 4A and 4B illustrate the principle of operation of a doubly labeled molecular beacon and of a singly labeled hairpin probe, respectively, as described in Example 6.

Probes are single-stranded nucleic acid molecules that possess a stem-and-loop structure (see FIG. 4A). The loop portion of the molecule is a probe sequence that is complementary to a predetermined sequence in the target nucleic acid. The stem is formed by annealing of the two complementary arm sequences that are on either side of the probe sequence, and the arm sequences are unrelated to the target sequence.

A fluorophor is attached to the end of one arm and a nonfluorescent quencher moiety is attached to the end of the other arm. The stem structure is used to keep the fluorophor and the quencher in close proximity to each other and to ensure efficient quenching of the fluorophor by fluorescence resonance energy transfer (FRET) in the isolated probe. When the probe hybridizes to a target molecule, it forms a hybrid that is longer and, hence, more stable than the hybrid stem structure. The probe undergoes a spontaneous conformational change that forces the arm sequences apart and causes the fluorophor and the quencher to separate. Thus, FRET is eliminated upon hybridization of the probe with the target and the fluorophor can now emit a detectable fluorescent signal.

Figure 4B:
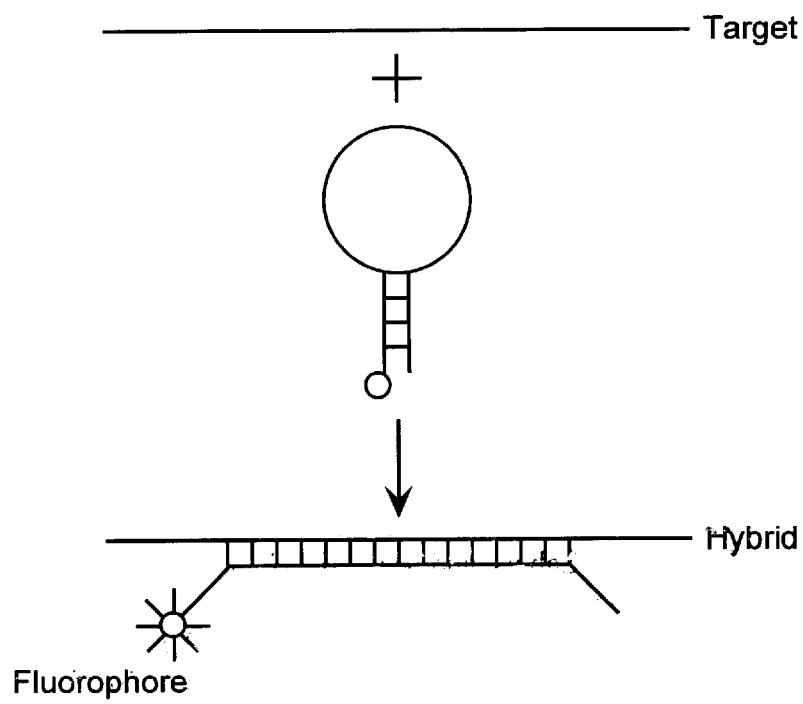

This same design can be used without the need for a separate quenching dye (see FIG. 4B). The hairpin probe is labeled with a quenchable dye at one terminus. When in the hairpin structure, the quenchable dye fluorescence is essentially completely quenched because the terminal nucleotide is part of a duplex. When the beacon hairpin duplex is broken and the long duplex with the target is formed the quenchable dye-labeled terminus is no longer in a duplex and quenching of the dye fluorescence is overcome.

Free, unhybridized probes do not emit a detectable radiation and, accordingly, it is not necessary to separate probes hybridized to the target from unhybridized probes. Accordingly, single label quenching molecular beacons can be used for the detection of nucleic acids in homogeneous assays and in living cells, as well as for real time monitoring of assays in which nucleic acids are being synthesized, e.g., polymerase chain reactions.

EXAMPLE 7

Ligase Chain Reaction

Figure 5:
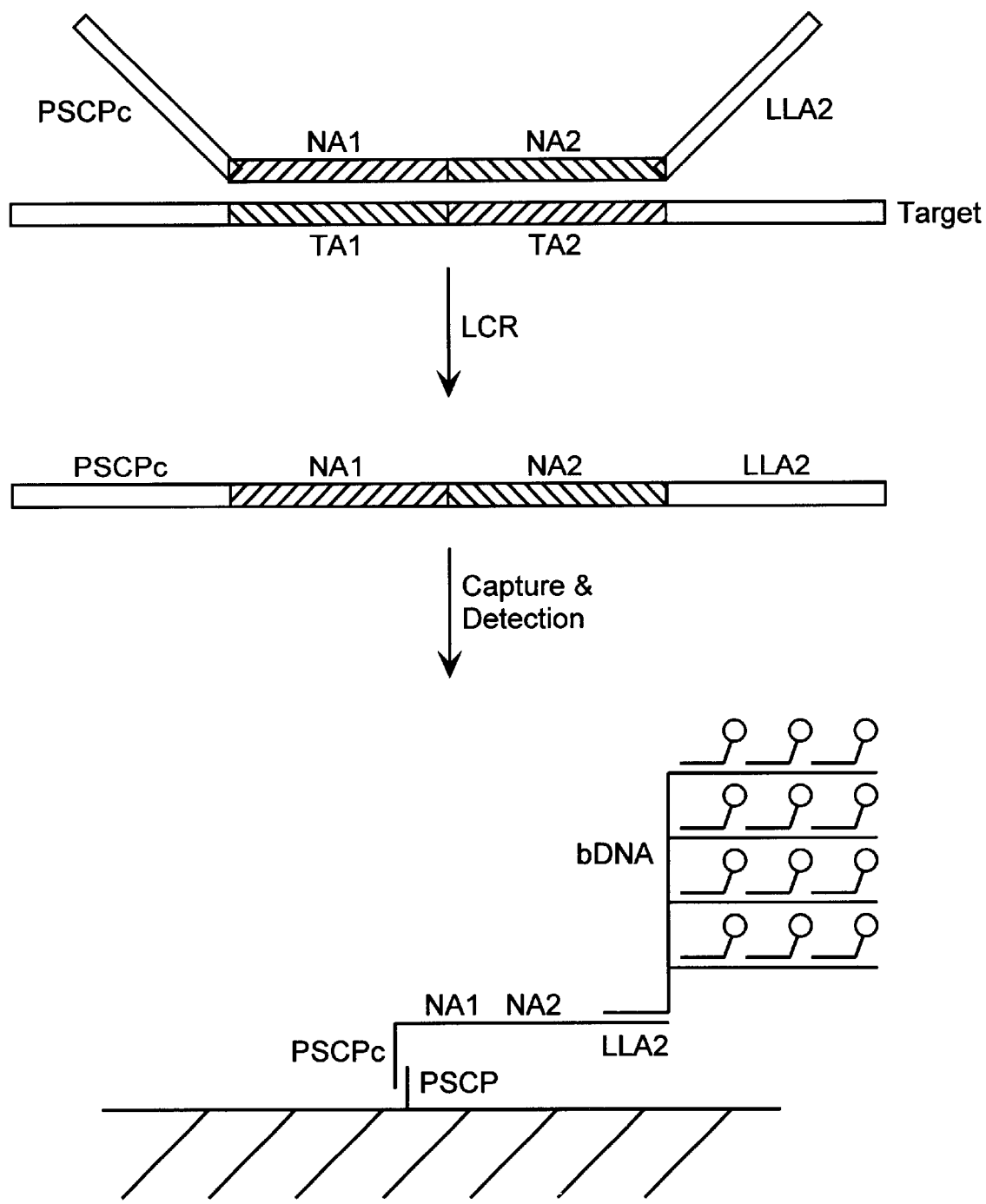
FIG. 5 is an illustration depicting the detection and amplification of a single base change using the LCR fluorescence assay as described in Example 7.

In this method, illustrated in FIG. 5, a probe containing the two sequences PSCPc (5'-TTT CTC TTG GAA AGA AAG TGA AGT G-3') SEQ ID NO:8 and NA1 (a first nucleic acid sequence complementary to a first portion of a target sequence TA1) is specifically linked to another probe containing the sequences NA2 (a second nucleic acid sequence complementary to a second portion of a target sequence TA2) and LLA2 (the label extender sequence in the Chiron Quantiplex assay) when both probes are hybridized to a target. Oligonucleotide products are exponentially amplified by thermal cycling of the ligation reaction in the presence of a second set of adjacent oligonucleotides that are complementary to the first and the target. After the amplification the ligated probe product, PSCPc-NA1-NA2-LLA2, is captured on a solid substrate, e.g., a plate or a bead, to which is attached a oligomer containing the PSCP sequence via the PSCPc tail. The presence of the LLA2 tail sequence makes it possible to use a bDNA amplification assay with a label probe conjugated through a linker to a quenchable dye to detect the ligation product. (see FIG. 5).

EXAMPLE 8

Quenchable Fluorescent Oligomers

Incorporation of quenchable dye-labeled nucleotide triphosphates during enzymatic DNA/RNA synthesis produces a strongly fluorescent oligomer. However, the dye will be quenched when the oligomer is in a double- or triple-stranded hybrid complex. Separation of the strands by, e.g., exposure to increased temperature, will result in a strong fluorescent signal from the incorporated labeled nucleotides. Such oligomers are useful in nucleic acid hybridization assays.

EXAMPLE 9

Strand Displacement Assay

Ellwood et al. (1986) *Clin Chem.* 32:1631–1636 describe an assay system for distinguishing between a native oligonucleotide strand and one containing a point mutation. In this system, a long probe oligomer is hybridized to a shorter labeled oligomer (20–50 nucleotides). The hybrid is mixed with the sample believed to contain the mutant strand; any target DNA present in the sample will displace the labeled oligomer. To quantitate the results, the displaced oligomer must be separated from the hybrids by a suitable technique. This simple technique is potentially of great value for quantitation of nucleic acid species, but it is important to have a simple, reliable method of separation.

Figure 6:
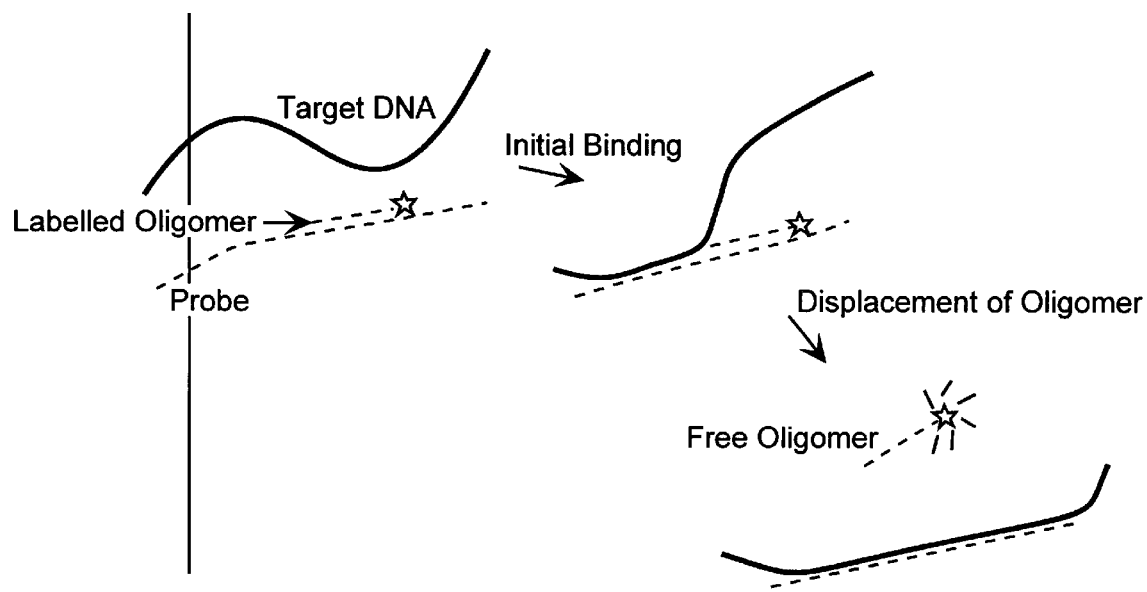
FIG. 6 is a schematic representation of a strand displacement DNA probe assay as described in Example 9.

Using a quenchable dye-labeled probe the Ellwood et al. system will work without separation, i.e., it will work as a homogeneous assay, since in the double-stranded DNA form the quenchable dye fluorescence is quenched, whereas after displacement it will be fluorescent (see FIG. 6).

EXAMPLE 10

Point Mutation Detection

Saiki et al. (1985) *Biotechnology* 3:1008–1012, which is incorporated herein by reference, describes a method for detecting a gene containing a point mutation. A short $^{32}$P-labeled oligonucleotide complementary to a target sequence in the wild type gene is prepared and hybridized to a sample DNA, thereby creating a new restriction enzyme cleavage site. If the sample contains a gene having a point mutation within the target sequence, the mutation results in, for example, a mismatch base pair upon formation of the labeled oligonucleotide-mutant gene hybrid complex. The presence of the mismatch base pair interferes with cleavage of the oligonucleotide-mutant gene hybrid duplex by the restriction enzyme. Any nonhybridized labeled oligonucleotide is blocked by the addition of a mutant-specific oligomer, i.e., an oligomer that hybridizes to the labeled oligonucleotide to form a complex that does not have the restriction enzyme cleavage site. Addition of the appropriate restriction enzyme will cut only the wild type gene, releasing a short labeled single-stranded fragment of the oligomer into solution. Separation by electrophoresis and autoradiography will reveal whether the label is on a short fragment or, as in the case of the mutant allele, still bound to the gene.

Figure 7:
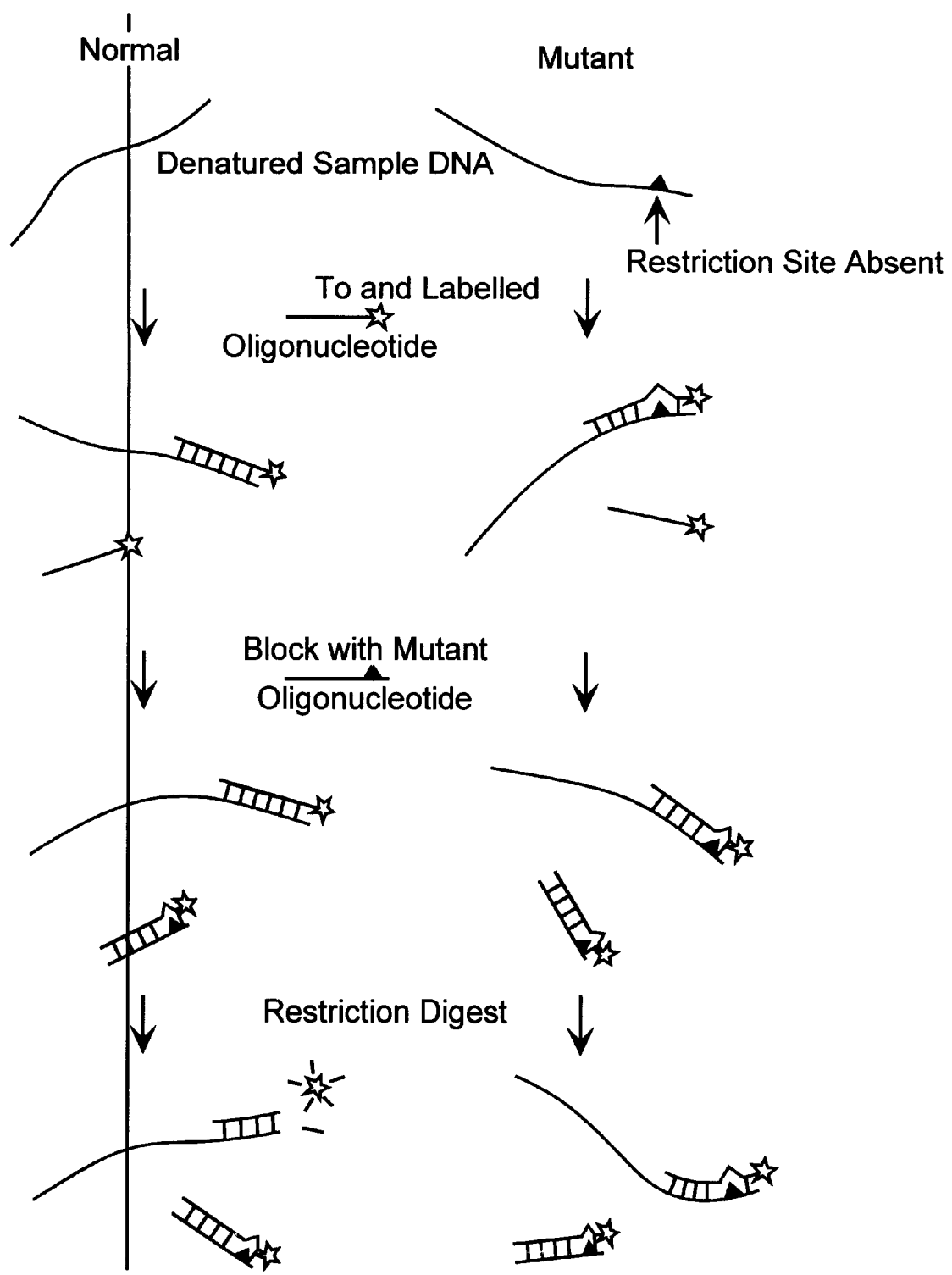
FIG. 7 is a schematic representation of a hybridization assay for detecting a point mutation as described in Example 10.

Using a quenchable dye-labeled probe the method can be modified to be conducted entirely in solution phase, without requiring component separation. After hybridization of the probe to the wild type gene, the restriction digest will release part of the labeled probe in a short duplex with a portion of the target. This duplex can be designed to be quite short and of low stability resulting in spontaneous strand separation. The quenching of the quenchable dye fluorescence in the duplex is overcome and a detectable signal will result. If the mutant gene is present, the detectable signal will be substantially reduced or eliminated. Excess quenchable dye-labeled probe remains hybridized to the mutant-specific oligomer, thus the dye signal is quenched and undetectable (see FIG. 7).

EXAMPLE 11

Point Mutation Detection

Figure 8:
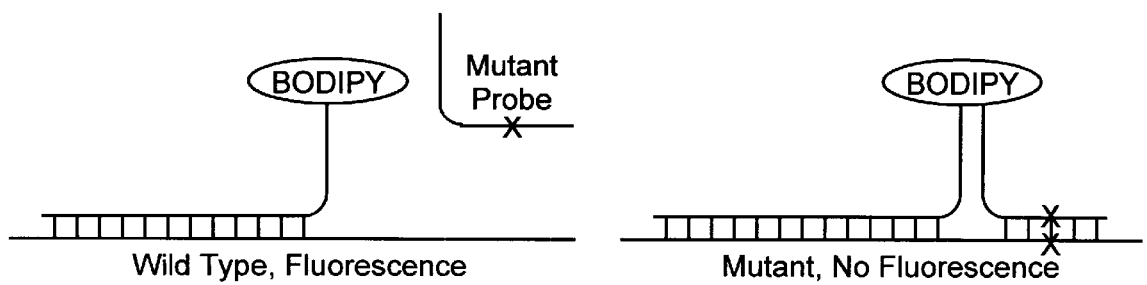
FIG. 8 is a schematic representation of a hybridization assay for detecting a point mutation as described in Example 11.

A second method for detecting a point mutation in a gene is illustrated in FIG. 8. In this method, a first probe is prepared having a first nucleic acid sequence that is complementary to a native target nucleic acid sequence in a gene. The target nucleic acid sequence is chosen to be in close proximity or adjacent to, and either upstream (as illustrated) or downstream from, a sequence suspected of containing a point mutation. The first probe has a second nucleic acid sequence complementary to a nucleic acid sequence in a second probe. The second nucleic acid sequence of the first probe is covalently linked to a quenchable dye molecule. A second probe is provided having a third nucleic acid sequence that is complementary to either the wild type nucleic acid sequence in the gene or, optionally, the nucleic acid sequence in the gene harboring the point mutation, as shown in FIG. 8. The wild type or mutant nucleic acid sequence in the gene is downstream (as illustrated) or upstream from the native target nucleic acid sequence. The second probe has a fourth nucleic acid sequence that is complementary to the second nucleic acid sequence of the first probe.

The assay can be conducted using, for example, two alternative protocols. In a first alternative, the gene of interest is incubated with the first probe under hybridizing conditions to form a gene-first probe hybrid complex. The gene-first probe hybrid complex is then incubated with the second probe in which the third sequence is either complementary to the wild type sequence or complementary to the mutant nucleic acid sequence in the gene of interest (see FIG. 8). If the gene contains a wild type sequence and the second probe is complementary to the mutant sequence, the gene-first probe hybrid complex will not hybridize to the second probe and the emission radiation from the quenchable dye compound will not be affected. If the gene contains a mutant sequence and the second probe is complementary thereto, a gene-first probe-second probe complex will be formed and the emission radiation from the dye will be substantially quenched. Thus, a decrease in signal emission indicates the presence of a point mutation.

In a second alternative, the assay can be conducted using a second probe having a third sequence that is complementary to the wild type sequence. In this case, a decrease in signal emission indicates the presence of the wild type sequence, but not when the gene contains a mutant nucleic acid sequence.

EXAMPLE 12

High Resolution Fiber Fluorescent In Situ Hybridization Optical Mapping

High Resolution Fiber Fluorescent In Situ Hybridization (FISH) Optical Mapping is an extension of the methodology developed in the laboratory of David Schwartz (see, e.g., Schwartz et al. (1997) *Curr. Opin. Biotechnol.* 8:70–74, and references cited therein; Samad et al. (1995) *Genome Res.* 5:1–4, and references cited therein; Meng et al. (1995) *Nat. Genet.* 9:432–438; and Cai et al. (1995) *Proc. Natl. Acad. Sci. USA* 92:5164–5168).

DNA is attached to a silanized coverslip in an elongated configuration. Once bound and stretched, the DNA is available for hybridization. Similar methodologies have been reported, e.g., Weier et al. (1995) *Human Molec. Genet.* 4:1903–1910, in which the ability to label stretched DNA molecules with sequence-specific labels by hybridization with biotin- and digoxigenin-labeled probes was demonstrated. However, multiple layers of fluorescence-labeled antibodies or fluorescence-labeled avidin molecules were required to generate a detectable fluorescent signal. The experiments described in this Example demonstrate the utility of branched DNA to label DNA in a sequence-specific manner, thereby obviating the need for multiple layers to detect specific regions of DNA.

A. λ DNA was labeled by hybridization using probes and the protocol reported by Weier et al for confirmation purposes. The lengths of the DNA restriction fragments were compared with reported results.

B. A model system was constructed to detect the HIV gag/pol region within a larger molecule. HIV gag/pol DNA was inserted into λGT10 phage at the unique EcoRI site. The two methods of detection (Weier et al. vs. bDNA) were compared.

In the first method, probes were synthesized using random primer protocols. The gag/pol region was hybridized with probes labeled with digoxigenin followed by detection with rhodamine-labeled anti-digoxigenin antibody and Texas red-labeled anti-sheep antibody. The λ DNA was hybridized with fluorescein-labeled probes followed by detection with anti-fluorescein antibody and fluorescein-labeled anti-mouse antibody in multiple layers.

In the second method, bDNA technology was used to label the HIV portion of the λGT10 construct followed by counterstaining the λ DNA with oxazole yellow homodimer (YOYO; Glazer et al. (1992) *Nature* 359:359). The results of the hybridizations were analyzed using IP Labs System software.

Fiber FISH mapping of λDNA: The 6 kb HindIII fragment of λ was mapped with anti-digoxigenin Texas Red antibody and appeared as red spots along the FITC-labeled backbone. Fiber FISH mapping was able to map the 6 kb fragment within 2 kb of the actual map position.

Fiber FISH mapping of GT10/HIV DNA: The 2.8 kb HIV fragment was mapped with anti-digoxigenin Texas Red antibody and appeared as red spots along the FITC backbone. Fiber FISH mapping was able to map the 2.8 kb fragment within 1 kb of the actual map position.

Fiber FISH bDNA mapping of GT10/HIV DNA: The HIV fragment was mapped with bDNA Texas Red-label probe and appear as red spots along the YOYO labeled backbone. Using bDNA the HIV fragment was mapped to within 1 kb of the predicted map position comparable to the fiber FISH mapping.

These results demonstrate the usefulness of bDNA in mapping small regions of DNA on a large backbone. Not only was the time to completion greatly shortened using bDNA (1 day or less) but the fluorescence signal using bDNA was considerably higher.

EXAMPLE 13

Use of bDNA Signal Amplification in Flow Cytometry

The flow cytometry assay uses reagents identical to those used in microwell-format bDNA assays with the exception of the solid phase and the labeled probe. In the flow cytometry technique, microparticles (latex beads) are derivatized with capture oligonucleotide. Following signal amplification with bDNA and a fluorescent reporter probe, the flow cytometer measures the fluorescence of the beads in the assay mixture. Unbound reporter molecules or particles of any size other than that of the beads (about 3 µm) are not detected. After signal amplification, the fluorescence of beads that have captured a single target molecule is clearly separated from that of beads that have not captured a target.

Thus, novel methods for generating a target-dependent signal in nucleic acid hybridization assays and other methods that involve the hybridization of a labeled oligomer to its complement have been disclosed. In addition, a oligomer-dye conjugate has been disclosed. Although preferred embodiments of the subject invention have been described in some detail, it is to be understood that obvious variations can be made without departing from the spirit and the scope of the invention as defined by the appended claims.

We claim:
1. A method for detecting an oligonucleotide of interest in a sample, comprising:
   (a) providing a first oligonucleotide probe comprising (i) a first nucleic acid sequence complementary to a nucleic acid sequence in the oligonucleotide of interest, and (ii) a label wherein the label is a fluorescent dye that comprises a dipyrrometheneboron difluoride compound that, when the probe is in single-stranded, non-hybridized form, provides detectable emission radiation that, when the probe hybridizes to a complementary nucleic acid strand, is substantially quenched;
   (b) combining the first oligonucleotide probe with the sample suspected of containing the oligonucleotide of interest under hybridizing conditions to form a probe-oligonucleotide of interest hybrid complex, while monitoring emitted radiation from the first oligonucleotide probe; and
   (c) subsequent to step (b), correlating any change in emitted radiation with the presence or quantity of the oligonucleotide of interest.

2. The method of claim 1, wherein the dye has the chemical structure

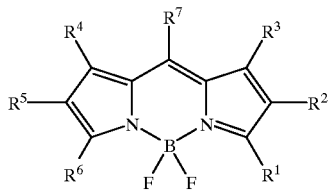

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX=CY—Z wherein X, Y and Z are independently halogen, $C_1$–$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;
   or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

3. The method of claim 2, wherein the dye is

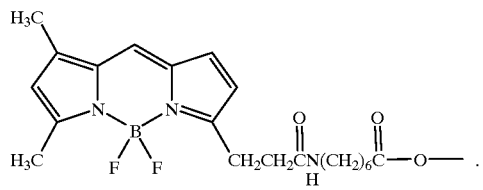

4. The method of claim 1, wherein the label is coupled directly to the probe.

5. The method of claim 1, wherein the label is coupled indirectly to the probe.

6. The method of claim 5, wherein the label is coupled to the probe through a linker substantially incapable of specifically hybridizing with a nucleic acid sequence in the oligonucleotide of interest.

7. The method of claim 6, wherein the linker is a nucleic acid sequence.

8. In a solution phase sandwich hybridization assay for detecting a nucleic acid analyte in a sample, comprising (a) binding the analyte indirectly to a solid support, (b) labeling the analyte and (c) detecting the presence of label on the support, the improvement which comprises:
   incorporating a label probe system comprising (i) a label extender molecule having a first segment L-1 capable of hybridizing to a nucleic acid sequence in the analyte and a second segment L-2, (ii) an amplification multimer containing a nucleic acid sequence M-1 capable of hybridizing to nucleic acid sequence L-2; and a plurality of identical oligonucleotide subunits containing nucleic acid sequences M-2 capable of hybridizing to label probe, (iii) a single-stranded label probe comprising a nucleic acid sequence L-3 capable of hybridizing to M-2 and a quenchable fluorescent dye coupled to the probe through a linker incapable of specifically hybridizing with a nucleic acid sequence in the analyte, the label extender, the amplification multimer or a target nucleotide sequence, wherein the quenchable fluorescent dye provides detectable emission radiation that is substantially quenched upon hybridization of the label probe to a complementary nucleic acid strand and the quenchable fluorescent dye comprises a dipyrrometheneboron difluoride compound.

9. The assay of claim 8, wherein the dye has the chemical structure

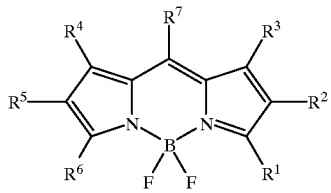

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX═CY—Z wherein X, Y and Z are independently halogen, $C_1$–$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

10. The assay of claim 9, wherein the dye is

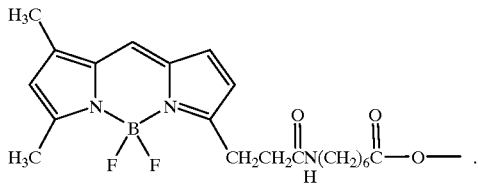

11. The assay of claim 8, wherein the linker is a nucleic acid sequence.

12. An oligonucleotide probe comprising (i) a nucleic acid sequence complementary to a nucleic acid sequence in an oligonucleotide of interest, and (ii) a label, wherein the label is a fluorescent dye that comprises a dipyrromethenboron difluoride compound that, when the probe is in single-stranded, nonhybridized form, provides a detectable fluorescent signal that, when the probe hybridizes to a complementary nucleic acid strand, is substantially quenched wherein the label is coupled to the probe through a linker comprised of a nucleic acid sequence that is substantially incapable of specifically hybridizing with a nucleic acid sequence in the oligonucleotide of interest.

13. The oligonucleotide probe of claim 12, wherein the dye has the chemical structure

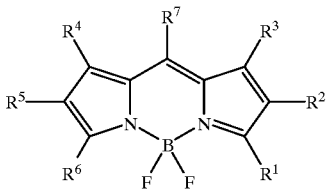

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX═CY—Z wherein X, Y and Z are independently halogen, $C_1$–$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R_5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

14. The oligonucleotide probe of claim 13, wherein the dye is

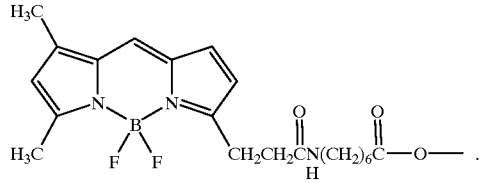

15. The method of claim 1, wherein:
the oligonucleotide of interest is a wild type gene and the nucleic acid sequence in the oligonucleotide probe is complementary to a target sequence in a wild type gene, wherein:
(i) formation of a hybrid duplex between the oligonucleotide probe and the target sequence in the wild type gene creates a site cleavable by a specific restriction enzyme;
(ii) formation of a hybrid duplex between the oligonucleotide probe and a point mutation-containing target sequence in a variant of the wild type gene does not create a site cleavable by the restriction enzyme;
(iii) step (b) comprises
incubating the oligonucleotide probe with a sample suspected of containing the variant of the wild type gene to form a variant-probe hybrid;
adding to the sample an oligomer capable of hybridizing to the oligonucleotide probe to form a hybrid complex that does not contain the restriction enzyme cleavage site; and following the addition of the oligomer, adding the restriction enzyme to the sample.

16. The method of claim 15, wherein the dye has the chemical structure

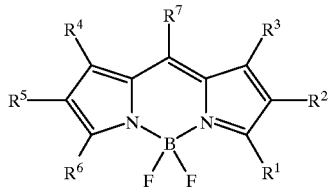

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX=CY—Z wherein X, Y and Z are independently halogen, $C_1$-$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

17. The assay of claim 16, wherein the dye is

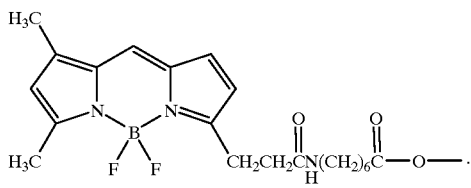

18. A method for detecting an oligonucleotide of interest in a sample, comprising:
   (a) providing a first oligonucleotide probe comprising (i) a first nucleic acid sequence complementary to a corresponding first nucleic acid sequence in the oligonucleotide of interest, and (ii) a label, wherein the label is a fluorescent dye that comprises a dipyrrometheneboron difluoride compound bound directly or indirectly to the 5' terminal nucleotide of the probe which, when the probe is in single-stranded, nonhybridized form, provides detectable emission radiation that is substantially quenched when the probe hybridizes to a complementary nucleic acid strand;
   (a') providing an oligonucleotide primer, wherein the primer is complementary to a second sequence in the oligonucleotide of interest and further wherein the corresponding first nucleic acid sequence of the oligonucleotide of interest is downstream from the second nucleic acid sequence in the oligonucleotide of interest;
   (b) incubating the first oligonucleotide probe and the primer with a sample containing the oligonucleotide of interest under conditions in which the first oligonucleotide probe and the primer hybridize to the oligonucleotide of interest;
   (b') adding an enzyme to the sample under conditions wherein the enzyme has 3' polymerase activity and 5' nuclease activity, whereby the detectable emission radiation is increased.

19. The method of claim 18, wherein the dye has the chemical structure

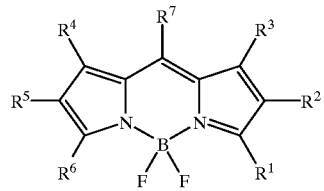

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX=CY—Z wherein X, Y and Z are independently halogen, $C_1$-$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

20. The assay of claim 19, wherein the dye is

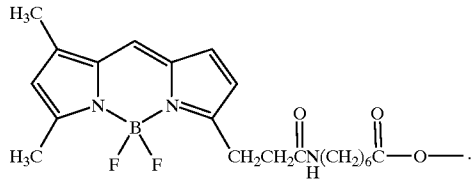

21. A method for detecting an oligonucleotide of interest in a sample, comprising:
   (a) providing a first oligonucleotide probe comprising (i) a first nucleic acid sequence complementary to a corresponding first nucleic acid sequence in the oligonucleotide of interest, and (ii) a label, wherein the label is a fluorescent dye that comprises a dipyrrometheneboron difluoride compound which, when the probe is in single-stranded, nonhybridized form, provides detectable emission radiation that is substantially quenched when the probe hybridizes to a complementary nucleic acid strand;

(a') providing a second oligonucleotide prove comprising a second nucleic acid sequence complementary to the corresponding first nucleic acid sequence in the oligonucleotide of interest;

(b) combining the first oligonucleotide probe with the sample suspected of containing the oligonucleotide of interest under hybridizing conditions to form a first probe-oligonucleotide of interest hybrid complex, while monitoring emitted radiation from the first oligonucleotide probe; and combining the first probe-oligonucleotide of interest hybrid complex formed in step (b) with the second oligonucleotide probe under conditions that the first oligonucleotide probe will be displaced from the first probe-oligonucleotide of interest complex, while monitoring emitted radiation from the first oligonucleotide probe.

22. The method of claim 21, wherein the dye has the chemical structure

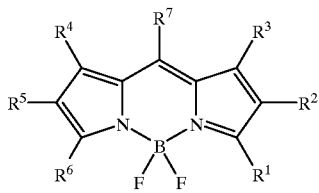

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX=CY—Z wherein X, Y and Z are independently halogen, $C_1$–$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

23. The method of claim 22, wherein the dye is

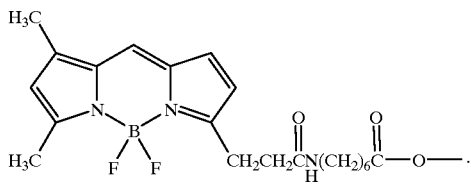

24. A method for detecting an oligonucleotide of interest in a sample, comprising:
(a) providing an oligonucleotide probe that comprises a single-stranded nucleic acid molecule comprising first and second complementary nucleic acid sequences flanking a third nucleic acid sequence that forms a loop structure when the first and second complementary nucleic acid sequences hybridizes with one another to form a stem structure, wherein the third nucleic acid in the loop structure comprises a nucleic acid sequence complementary to a nucleic acid sequence in the oligonucleotide of interest, and wherein the probe is singly labeled with a label, wherein the label is a fluorescent dye that comprises a dipyrromethenboron difluoride compound that provides detectable emission radiation, and further wherein the label is such that when the first and second nucleic sequences are hybridized to form the stem structure, the emitted radiation is substantially quenched, and when the third nucleic acid sequence is hybridized to the oligonucleotide of interest and the first and second nucleic acid sequences are in nonhybridized form, provides detectable emission radiation.

25. The method of claim 24, wherein the dye has the chemical structure

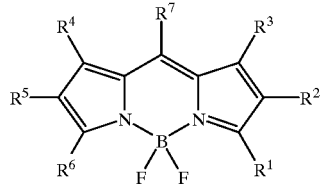

wherein $R_1$ through $R^7$ are independently selected from the group consisting of: hydrogen; halogen; alkyl; carboxyalkyl; acyl; aryl; arylalkyl; sulfonyl; formyl; substituted ethenyl having the formula —CX=CY—Z wherein X, Y and Z are independently halogen, $C_1$–$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryl, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

26. The method of claim 25, wherein the dye is

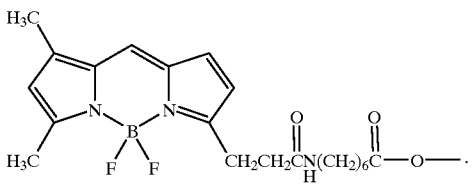

27. A method for detecting an oligonucleotide of interest in a sample, comprising:
(a) providing a first oligonucleotide probe comprising (i) a first nucleic acid sequence complementary to a corresponding first nucleic acid sequence in the oligonucleotide of interest, (ii) a second nucleic acid sequence complementary to a third nucleic acid sequence in a second probe, and (iii) a label, wherein the label is a fluorescent dye that comprises a dipyrromethenboron difluoride compound which, when the probe is in single-stranded, nonhybridized form, provides detectable emission radiation that is substantially quenched when the probe hybridizes to a complementary nucleic acid strand;
wherein the corresponding first nucleic acid sequence in the oligonucleotide of interest is adjacent to a second nucleic acid sequence in the oligonucleotide of interest, wherein the second nucleic acid sequence in the oligonucleotide of interest is either a wild type nucleic acid sequence or a nucleic acid sequence containing a point mutation, and wherein the method further comprises
(a') providing a second oligonucleotide probe, having third and fourth nucleic acid sequences, wherein the third nucleic acid sequence is complementary to either the wild type or the mutant second nucleic acid sequence in the oligonucleotide of interest and the fourth nucleic acid sequence is complementary to the second nucleic acid sequence in the first oligonucleotide probe;
(b) combining the first oligonucleotide probe with the sample suspected of containing the oligonucleotide of interest under hybridizing conditions to form a first probe-oligonucleotide of interest hybridization complex, while monitoring emitted radiation from the first oligonucleotide probe,
(b') incubating the second oligonucleotide probe with the first probe-oligonucleotide complex; and
(c) following step (b'), correlating any change in emitted radiation with the presence of the wild type sequence or the mutant sequence.

28. The method of claim 27, wherein the dye has the chemical structure

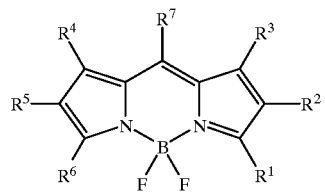

wherein $R^1$ through $R^7$ are independently selected from the group consisting of: hydrogen; halogen; alkyl; carboxyalkyl; acyl; aryl; arylalkyl; sulfonyl; formyl; substituted ethenyl having the formula —CX=CY—Z wherein X, Y and Z are independently halogen, $C_1$-$C_{10}$ alkyl, cyano, ester, amide, ethenyl, polyethenyl, aryl or heteroaryl; and —L—G, wherein L is a linking moiety and G is a reactive group enabling binding of the dye to an amino or carboxylic acid moiety;

or wherein (a) either $R^1$ and $R^2$, or $R^2$ and $R^3$, and/or (b) either $R^4$ and $R^5$, or $R^5$ and $R^6$, together form a benzene ring substituted with 0 to 4 substituents selected from the group consisting of hydrogen, halogen, cyano, sulfonyl, sulfonate, carboxyl, carboxylate, alkyl, perfluoroalkyl, alkoxy, alkylthio, nitro, amino, monoalkylamino, dialkylamino, alkylamido, aryl, aryloxy, heteroaryl, heteroaryloxy, arylamino, heteroarylamino, or arylamido, or wherein two ortho substituents are linked to form an additional such aromatic ring, with the proviso that at least one substituent within the group of $R^1$ through $R^7$ is heteroaryl, and at least a second substituent within the group of $R^1$ through $R^7$ is —L—G.

29. The method of claim 28, wherein the dye is

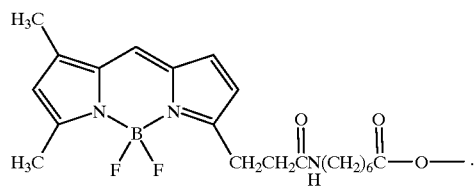

* * * * *